United States Patent [19]
Hoium et al.

[11] Patent Number: 5,951,484
[45] Date of Patent: Sep. 14, 1999

[54] METHOD OF NONINVASIVELY DETERMINING A PATIENT'S SUSCEPTIBILITY TO ARRHYTHMIA

[75] Inventors: Harold H. Hoium, Eden Prairie; Stephen J. Ryan, Chaska, both of Minn.

[73] Assignee: Harbinger Medical, Inc., Eden Prairie, Minn.

[21] Appl. No.: 09/127,231

[22] Filed: Jul. 31, 1998

Related U.S. Application Data

[60] Provisional application No. 60/054,701, Aug. 1, 1997, provisional application No. 60/072,936, Jan. 29, 1998, and provisional application No. 60/072,937, Jan. 29, 1998.

[51] Int. Cl.$^6$ ................................. A61B 5/04; A61B 5/05
[52] U.S. Cl. ........................................... 600/515; 600/518
[58] Field of Search .................................... 600/515–518; 607/10

[56] References Cited

U.S. PATENT DOCUMENTS

| | | |
|---|---|---|
| 4,537,201 | 8/1985 | Delle-Vedove et al. . |
| 4,552,150 | 11/1985 | Zacouto . |
| 5,117,834 | 6/1992 | Kroll et al. ............................. 600/518 |
| 5,555,888 | 9/1996 | Brewer et al. ........................... 600/515 |

*Primary Examiner*—William E. Kamm
*Assistant Examiner*—Carl H. Layno
*Attorney, Agent, or Firm*—Patterson & Keough, P.A.

[57] ABSTRACT

A method for detecting a patient's susceptibility to arrhythmias and cardiac tissue abnormality is disclosed. The method consists of using a computer, a display, software loaded onto the computer that generates graphical user interfaces (GUIs), an electronic interface, and a plurality of electrodes. The electronics interface is in electronic communication with the computer, and further in electronic communication with the electrodes that are placed by self-adhesion at predetermined locations on a test subject. According to one aspect of the invention, the method enables a user, typically a medical professional, to initiate, with minimal input, certain diagnostic tests involving observing and analyzing a series of QRS complexes, some of which are biased with a subpacing current, and others of which are unbiased. The signals are then compared, and the differences are analyzed to detect a patient's susceptibility to arrhythmias and cardiac tissue abnormality.

39 Claims, 37 Drawing Sheets

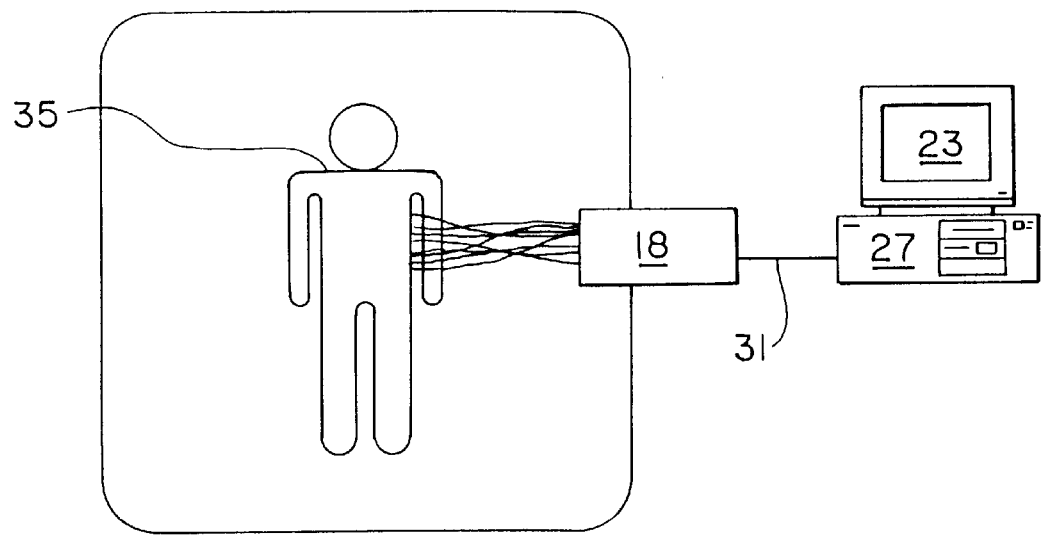
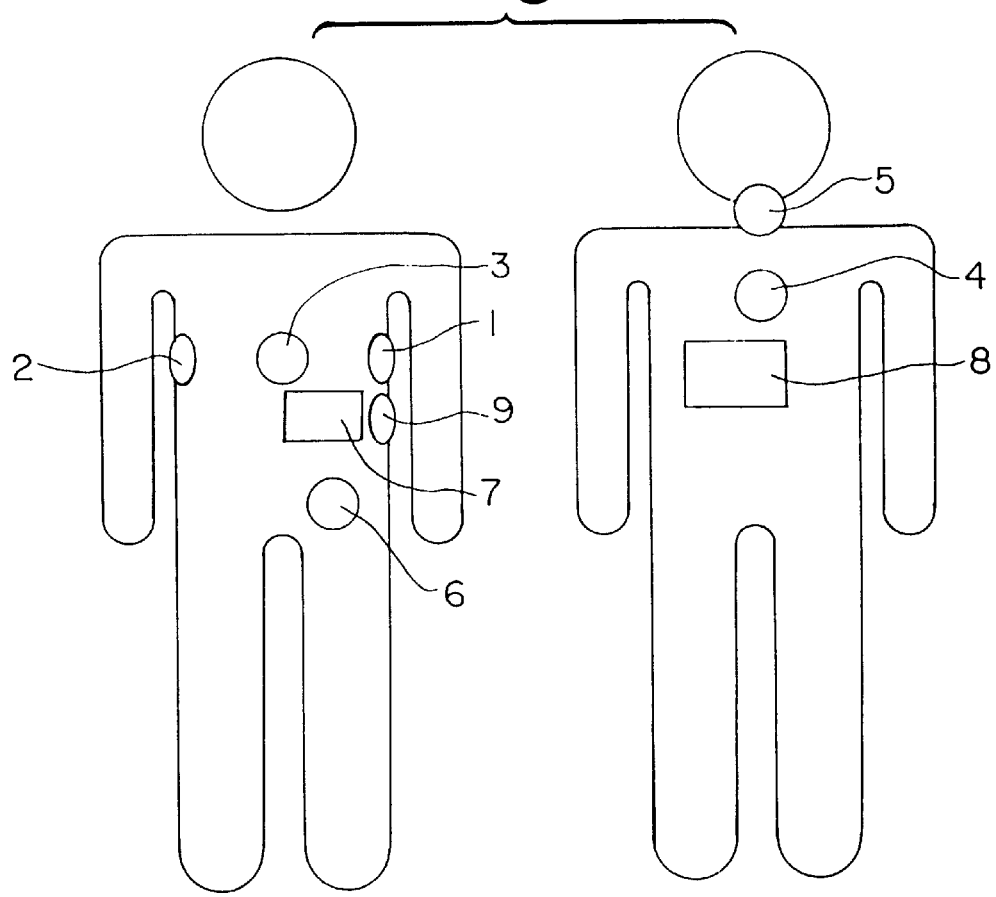

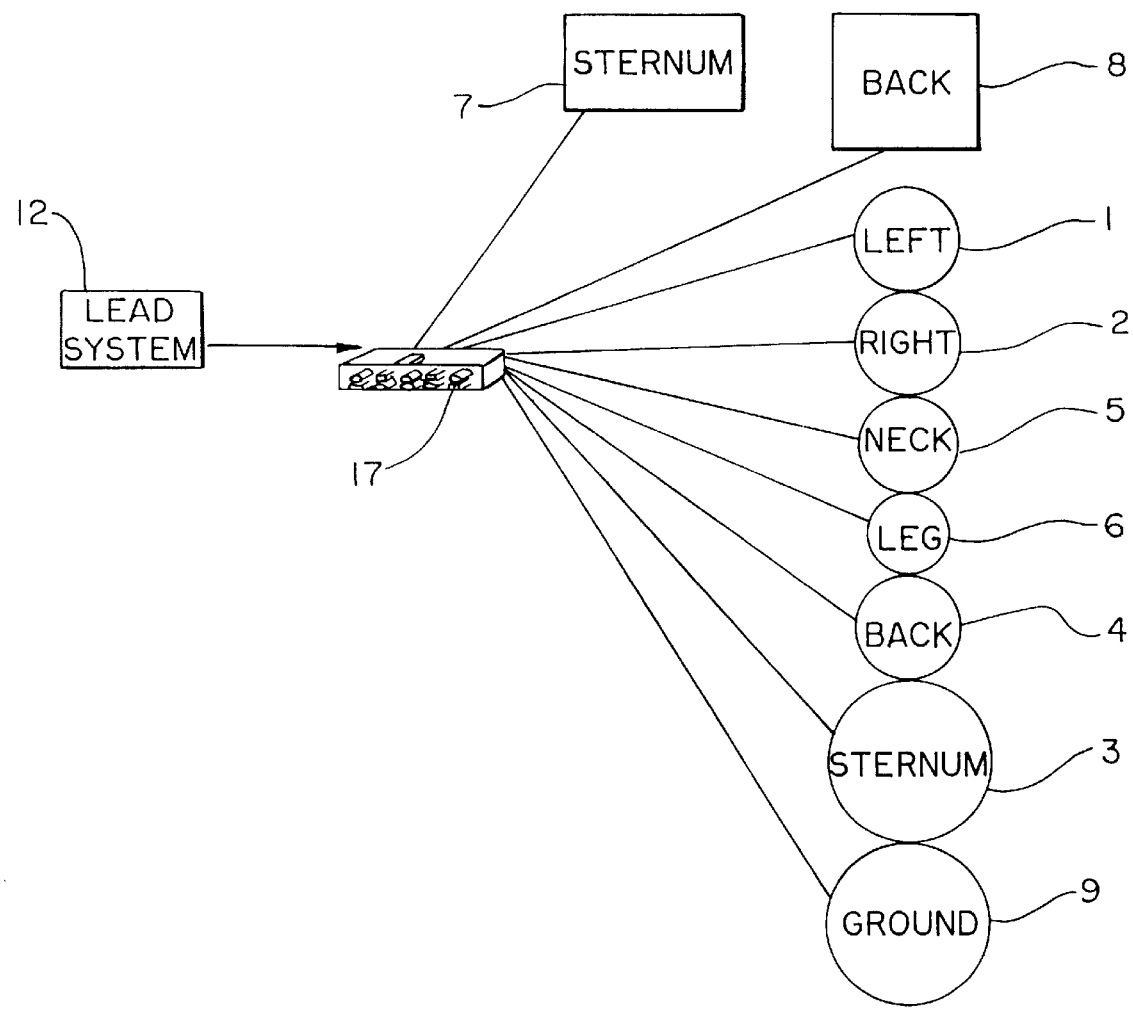

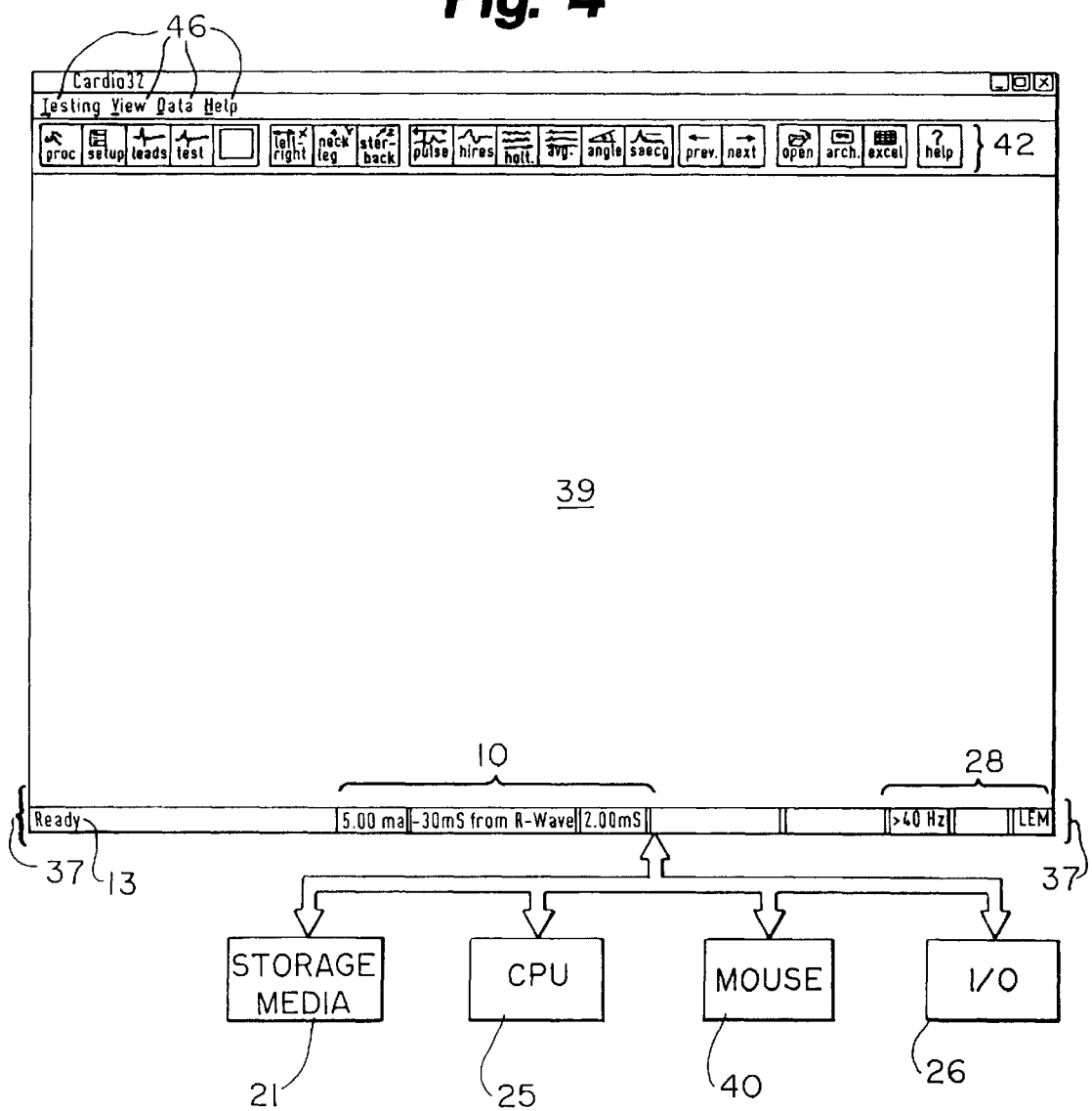

Fig. 27

```
Accessing Stored Subject Data
┌Test Information──────────┬─Bias Information──────┬─Subject Information──────────────┐
│Timestamp  Valid Bias Count│ uA    mS   Position  │ ID        Name (age/gend)       │
├───────────────────────────┼──────────────────────┼─────────────────────────────────┤
│03/12/97-14:41  15 (+/-10mS.)│5.00mA. 2.00mS. -30mS.│123456789AB Samuel Jones(52/m)  │
│03/12/97-14:26  15 (+/-10mS.)│5.00mA. 2.00mS. -30mS.│123456789AB Samuel Jones(52/m)  │
│03/12/97-13:41  15 (+/-15mS.)│5.00mA. 2.00mS. -30mS.│123456789AB Samuel Jones(52/m)  │
```

[ OK ]   [ Cancel ]

Fig. 28

Open

Look in: data

| 6GH004R | 6GH0142 | 6GH023G | 6GHC045 |
| 6GH006S | 6GH0162 | 6GHB581 | 6GHC059 |
| 6GH0089 | 6GH017F | 6GHB59A | 6GHC06R |
| 6GH0091 | 6GH018P | 6GHC00F | 6GHC081 |
| 6GH011E | 6GH0204 | 6GHC011 | 6GHC095 |
| 6GH012N | 6GH021D | 6GHC031 | 6GHC108 |

File name: 6GH004R          [ Open ]
Files of type: Harbinger Tests  [ Cancel ]

Fig. 29

Protocol Steps

Protocol Information

| Step # | Pulses | Sensitivity | Deviation | uA | mS | Position | Ramp |
|---|---|---|---|---|---|---|---|
| 1 | 30 | Low | 15 | 0.00 | 0.50 | -20 | Off |
| 2 | 30 | Low | 15 | 20.00 | 0.50 | -20 | Off |
| 3 | 30 | Low | 15 | 0.00 | 2.00 | -20 | Off |
| 4 | 30 | Low | 15 | 20.00 | 2.00 | -20 | Off |
| 5 | 30 | Low | 15 | 0.00 | 0.50 | 0 | Off |
| 6 | 30 | Low | 15 | 20.00 | 0.50 | 0 | Off |
| 7 | 30 | Low | 15 | 0.00 | 2.00 | 0 | Off |
| 8 | 30 | Low | 15 | 20.00 | 2.00 | 0 | Off |
| 9 | 30 | Low | 15 | 0.00 | 0.50 | 20 | Off |
| 10 | 30 | Low | 15 | 20.00 | 0.50 | 20 | Off |
| 11 | 30 | Low | 15 | 0.00 | 2.00 | 20 | Off |
| 12 | 30 | Low | 15 | 20.00 | 2.00 | 20 | Off |

69

OK    Cancel

Fig. 30

Select Protocol Step

Select Protocol Step

1    —158

OK —36

Cancel

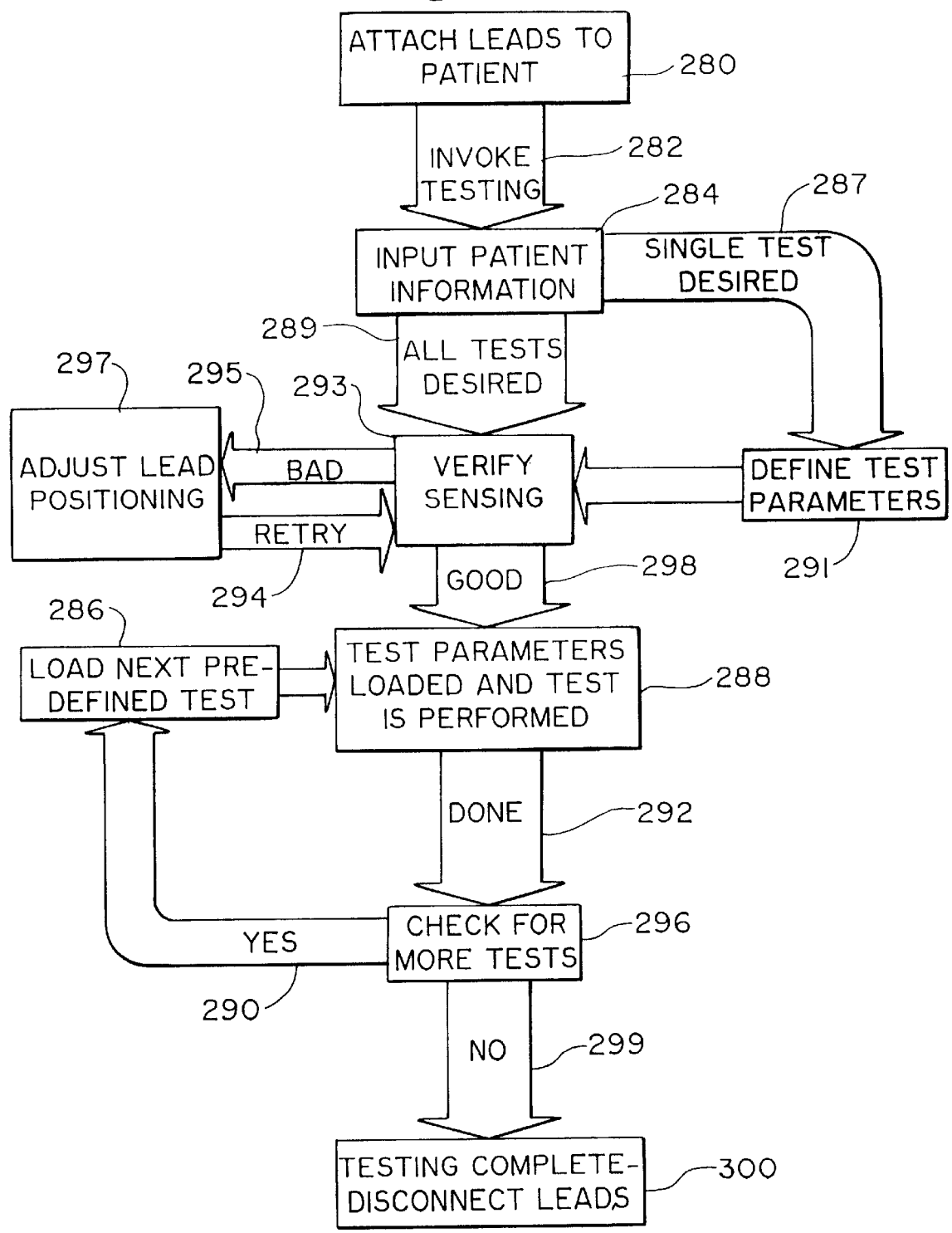

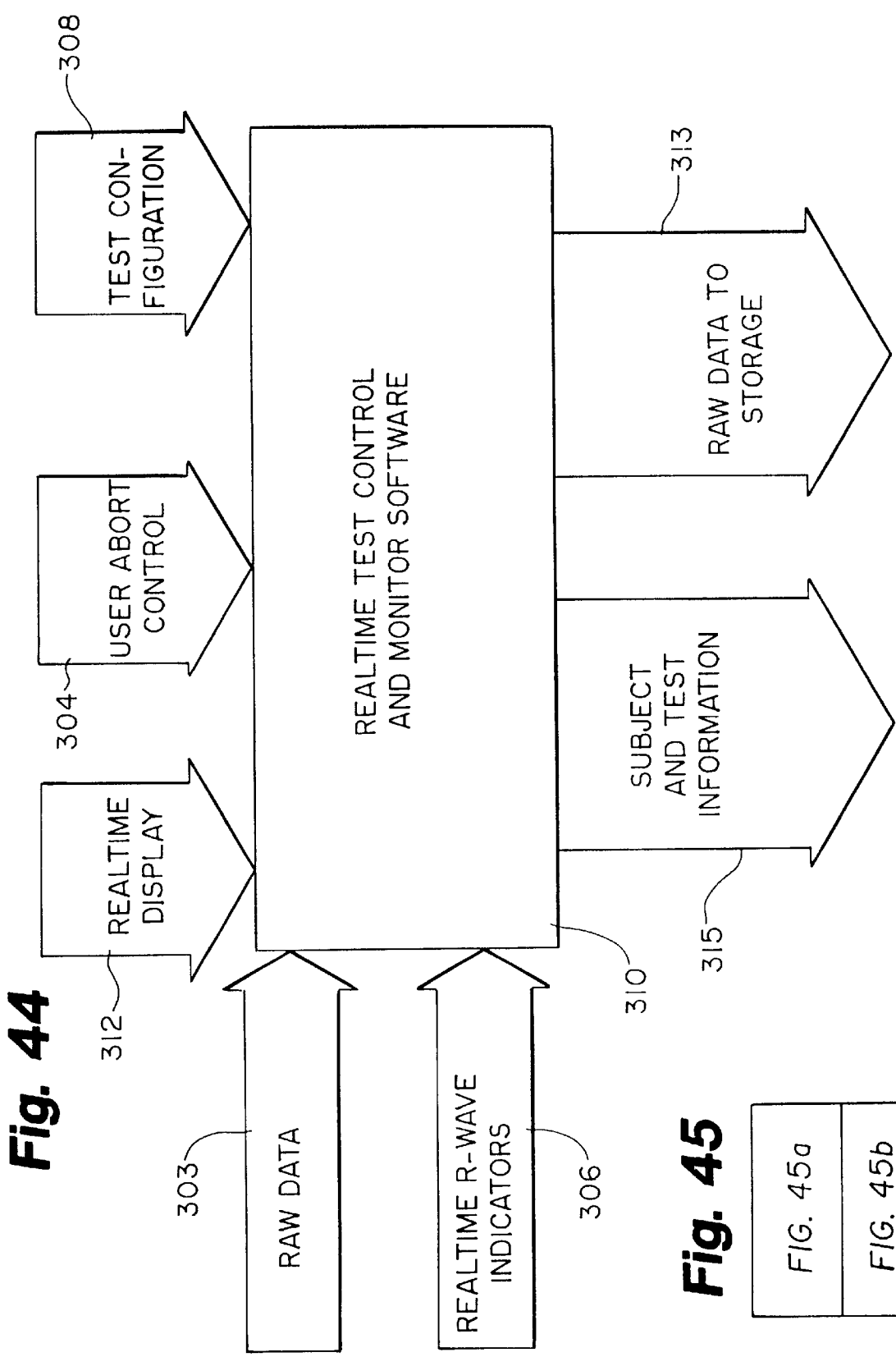

METHOD OF NONINVASIVELY DETERMINING A PATIENT'S SUSCEPTIBILITY TO ARRHYTHMIA

CROSS-REFERENCE TO RELATED APPLICATION

This application claims priority under 35 U.S.C. §119(e), to previously filed U.S. Provisional Patent Application Serial No. 60/054,701, filed Aug. 1, 1997; Ser. No. 60/072,936, filed Jan. 29, 1998; and Ser. No. 60/072,937, filed Jan. 29, 1998, the subject matter of which is incorporated herein by reference.

FIELD OF INVENTION

The invention relates to the detection of patients' susceptibility to arrhythmias and, more particularly, to various techniques for improving the detection of signals to achieve this goal.

BACKGROUND OF THE INVENTION

There are various devices known in the art for monitoring heart function. Many of these devices typically function by analyzing signals such as an electrocardiogram signal, which can be representative of heart function.

There is a need to identify patients at high risk for life-threatening arrhythmias.

Various means have been proposed for detecting patient susceptibility to arrhythmias. U.S. Pat. No. 5,117,834 discloses one method by which pulses of electromagnetic energy are injected into a patient and the changes in the patient's electrocardiographic signals caused by the injection are recorded. U.S. Pat. No. 5,351,687 is similar in concept to U.S. Pat. No. 5,117,834, but it describes use of a magnetic sensor for use in detecting the cardiographic signals. U.S. Pat. No. 5,555,888 discloses various means for adapting and automatically facilitating the assessment techniques and means similar to that shown in the above patents for determining patient susceptibility to arrhythmias.

Other techniques which are used to analyze cardiac signals for somewhat similar purposes include those known as t-wave altemans and signal-averaged electrocardiograms. Each of these techniques is limited in its application and utility by various factors which are overcome through use of the below described inventions.

SUMMARY OF THE INVENTION

The present invention provides a system and method of determining, through noninvasive means, a patient's susceptibility to arrhythmia. More specifically, this invention comprises various improvements to known innovations for optimizing detection of a patient's susceptibility to arrhythmias. This invention embodies numerous software and sequence improvements for applying this basic technology.

Another purpose of this invention is to provide hardware and software analysis means for detecting and amplifying relevant signals.

Another purpose of this invention is to provide for improved performance lead sets and the software to promote ease of attachment and removal from the patient and ease of connection of the lead system to the hardware.

A further object of this invention is to provide new combinations of electrode placement and use to promote better arrhythmia susceptibility diagnosis.

A further object of this invention is to provide a reduction in the size of necessary components to allow for hand-held system dimensions.

A further object of this invention is to provide a means for distinguishing between the signals from the X, Y, and Z directions as well as previously unused directional components of very low-level signal data.

Another object of this invention is to supply means for displaying of patient's waveforms and other data derived from the detected signals, as well as to provide various interfaces to communicate the data between the patient and physician or health care professional.

It is a further object of this invention to provide signal artifact reduction, and to provide a single point connector for the set of leads.

Another object of this invention is to provide improved lead materials for improved performance, as well as an improved lead effect modeling (LEM).

It is yet another object of this invention to provide amplifier circuitry that minimizes amplifier saturation and optimizes fast recovery.

DETAILED DESCRIPTION OF THE PREFERRED EMBODIMENTS

The invention provided is an improved method and system for detecting patients' susceptibility to arrhythmia and cardiac tissue abnormality in a noninvasive fashion. In FIG. 1, computer 27 is operably coupled to monitor 23, which is further closely coupled with electronic interface 18 via wire 31. Lead system 12 is connected between patient 35 and electronic interface 18.

FIG. 2 is a front and rear view of patient 35. In one preferred embodiment, lead system 12 consists of 9 lead wires. Advantageously, the lead system can be connected as shown in FIG. 2 for efficient and consistent setup of the invention. Typically, the lead system is preassembled with a predetermined number of leads having predetermined lengths. Although it is contemplated by this invention that the lead system can be preassembled with leads of different lengths to accommodate different room sizes and patent locations, among other factors, a general consideration is that the sensing leads and energy delivery leads are less than 9 feet in length to reduce possible induced noise. Further, the leads in lead system 12 are constructed from a low-impedance material, such as tin, sodium, silver, silver chloride, or other low-impedance material recognized as such by those skilled in the art. This construction assists in efficient delivery of subpacing energy for stimulation leads and increased sensitivity for sensing leads. The electrodes involved with energy delivery are advantageously shaped and sized for placement on the patient's body habitus to minimize signal quality reduction by avoiding muscle tissue.

FIG. 3 shows a more detailed view of one preferred embodiment of single-point connector 15 with 9 lead wires electronically coupled thereto. In this embodiment, each of the 9 lead wires is connected to one of 9 self-adhesive electrodes. The adhesive used on any specific electrode can differ depending on various factors, including where on patient 35 the electrode or patch is to be affixed and whether the electrode is reusable or disposable. In one preferred embodiment, electrode 1 is to be connected in the correspondingly-numbered position indicated in FIG. 2. Thus, for example, electrodes 1 and 2 are connected on patient 35 at the corresponding left and right mid-axillary lines, on a horizontal plane, at the level where the fifth intercostal space intersects the sternum. Electrode 3 is placed on the sternum. In this embodiment of the invention, electrode 4 is placed on patient 35 at the fifth intercostal space. Electrode 5 is a neck electrode and is attached generally at the back of the neck, as indicated on back view 2.2 of FIG. 2. Lead 6 is a left leg lead that will attach generally in the location on patient 35, as shown on front view 2.1 of FIG. 2. The larger, rectangular electrodes, electrodes 7 and 8, are attached in the pectoral area and back, respectively, as shown in FIG. 2. In one preferred embodiment, the generally pectorally-placed electrode 7 or patch has a skin contact surface area of at least 20 cm², and typically less than about 70 cm². The patches of lead system 12 can be constructed with different electrical characteristics to facilitate energy transfer and sensing.

Single-point connector 17 is configured to electronically mate with electronic interface 18. A top-level block diagram of electronic interface 18 is shown in FIG. 37. In one embodiment, single-point connector 17 advantageously couples 9 electroleads into one plug assembly. As can be seen in FIG. 3, one preferred embodiment is a stacked lead receptacle having at least two rows of lead connections that are identified with respect to each lead (also see FIG. 42). This advantageously provides for a more compact connector, and provides for rapid and efficient coupling and decoupling to electronics interface 18. In one preferred embodiment, the connector 15 is designed to be easily and rapidly coupled and decoupled with the electronics interface 18 by the use of only one hand. Advantageously, this allows for efficient setup and takedown of the invention. Patches 1 through 9 are premarked, as indicated on FIG. 3, to provide for simpler and more convenient placement on patient 35. Further, the lead system 12 comprises a reference lead 9. It is anticipated that the lead system 12 can be a single-use system or a disposable system to provide for a safe and sterile means by which to perform the tests provided by this invention. Further, reusing the lead system may create a higher impedance in the system, which may make the lead system 12 more susceptible to noise. In one preferred embodiment of the invention, a means is provided for determining whether the lead system has been previously used. This can be done by using a single-use-type adhesive. Another means for detecting previous use is creating a deformable tab on connector 17 that deforms on its first mating with electronic interface 18, and thereafter is not usable. Creating fusible links or breakable tabs to indicate the lead system has been previously used are an additional means, among others.

The electronics interface 18, by coupling with computer 27, allows for the injection of low-level electromagnetic energy into patient 35 to alter at least one cardiac signal. The energy is delivered at a subpacing threshold and is typically introduced externally, through patient 35's chest and into cardiac tissue. The subpacing energy is delivered just before a QRS complex event, as determined by the data gathered by the hardware and electronic interface 18, and as analyzed by the software. Electronic interface 18 and attached computer 27 function to process received signals, among other functions. The energy delivery leads are typically leads 7 and 8; however, it is anticipated that circumstances may arise where more or less than two energy delivery leads may be needed. In such cases, greater or fewer leads may be configured to delivery energy. Further, the number of sensing leads may be variable as well, depending on the needs and judgment of the medical professional administering the testing.

FIG. 31 depicts an exemplary QRS complex and related signals. P-wave 153 is the signal that typically precedes the actual QRS complex 130. The interval between the start of the P-wave and the beginning of QRS complex 130 is known as the PR interval 150. QRS complex 130 is typically made up of three distinct components: Q 117, which is typically the first negative signal; R 113, which is typically the first positive signal; and S 121, which is the first negative signal subsequent to R 113 signal. T segment 133 is typically defined as the more-or-less flat signal, or absence of signal, subsequent to recovery of the S 121 portion of QRS complex 130, prior to commencement of t-wave 146. The QT interval is typically defined as the portion of the signals commencing at the beginning of QRS complex 130 and ending after t-wave 146. J Joint 137 is typically defined as the end of the QRS complex and the beginning of the ST segment 133. The T-P interval (not indicated) is the time period from the end of the T-wave to the beginning of the next P-Wave. The entire cardiac cycle is P-Q-R-S-T.

The slight transcutaneous biosync or subpacing current is typically introduced by the invention at odd numbers of QRS complex normal sinus beats. Resulting QRS complexes are then compared to the even-numbered unbiased beats. By computer-implemented software, the distinguishable signal differences can then be calculated and displayed. Generally, differences are found between the biased and unbiased QRS complexes in patients with ventricular tachycardia and other indices of arrhythmia or cardiac tissue abnormality. It is anticipated that these input potentials would be extremely small, for example, less than 100 uV, and typically of a duration of less than about 100 mS. Such a current might involve visualization of a possible analog of late potentials throughout the QRS complex.

Computer 27 operates a graphical user interface (GUI) based software, which generally includes a tool bar, a status bar, a display area, and various drop-down menus. The principal GUI is depicted in FIG. 4. The GUI consists of display area 39, status bar 37, tool bar 42, and drop-down menus 46. Tool bar 42 contains button icons that represent shortcuts to many of the functions described below in association with drop-down means 46. Status bar 37 depicts the general status 13 of the software on the left-hand side, technical data 10 regarding the lead sensors and input current in the middle section, and frequency and protocol information 28 generally on the right-hand side. FIG. 4 illustrates a GUI in Microsoft Corporation's Windows 95™ operating system format. The GUI is generated by computer 27, which typically consists of mouse 40, CPU 25, display 23, a keyboard (not shown) operably attached to computer 27, and peripheral input/output devices 26, as well as storage media 21.

FIG. 5 depicts "Testing" drop-down menu 48 engaged. As revealed in FIG. 5, "Testing" drop-down menu 48 provides a series of options to perform testing provided for by this invention. If the "Performed Test Sequence" 50 is selected, the GUI of FIG. 6 is generated on display 23. Using mouse 40 or keyboard input, a preexisting patient may be selected from display area 39 of this GUI, or "New Patient" button 52 may be selected. Mouse 40 or keyboard input may be used to select all operable functions of the GUIs involved in this invention. If "OK" 36 is selected from the GUI of FIG. 36, subject information 41 is retrieved for the highlighted subject. "Cancel" 30 returns the operator to the view of the GUI of FIG. 4.

FIG. 7 depicts the informational GUI that appears if "New Patient" button 52 is selected. In the upper portion of the GUI represented in FIG. 7, subject information may be entered in box 44 which includes identification number (ID) 55 to associate with the patient, patient's Name 58, patient's Birthdate 64, Gender 66 of the patient, Race 80 of the patient, and any miscellaneous notes 85 that might be helpful during or after the patient's diagnostic sessions.

The lower portion of the GUI depicted in FIG. 7 includes six boxes where testing parameters are entered. The test duration box 90 is configured by the medical professional to indicate how many QRS complex signals will comprise the test. The options under the sensitivity input box 68 are low, medium, and high. This advantageously allows the sensitivity to be adjusted to correct over- or under-sensing caused by subject-to-subject variation in QRS amplitude and morphology. The next variable parameter is the deviation limit 87, which is entered in milliseconds in the correspondingly marked box. Deviation limit 87 allows the operator to eliminate inaccurately-positioned stimulations from post-processing. This can happen due to the predictive nature of pre-R-wave stimulation and the normal R-R interval variation (see FIG. 36). The operator identifies the allowable tolerance. Any pulses that are greater than this tolerance are eliminated from further processing. Also in FIG. 7 is pulse configuration box 33. In pulse configuration box 33, the low-current pulse can be configured to account for the different circumstances of the patient to be tested. The parameters or variables are current strength 72, width of the pulse 82 (in milliseconds), and temporal location 92 of the pulse with respect to the QRS complex. A one-millisecond Pulse Ramp Up 78 option is also available by checking the corresponding box on the GUI.

FIG. 8 depicts a GUI option screen where a simplified selection can be made for all available testing standard protocols. There, selection of "Yes" 11 invokes all currently defined standard protocols. These protocols are set up initially and invoke from this screen. This option advantageously allows testing without requiring the operator to set the specific parameters for each subject being tested. "No" 17 returns the user to the previously displayed GUI.

FIG. 9 is a GUI that appears on screen 23 to determine whether the professional is ready to verify the sensing of the electrodes attached to patient 35. "Yes" 36 will commence the sensor verification. "Cancel" 30 will return the operator to the previous screen. If default protocols are to be used on the patient, then the operator need not define the test parameters. The system will get these standard parameters from the internal disk (not shown) of computer 27.

If "Cancel" 30 is selected on the GUI of FIG. 7, any changes will be discarded and the performed test function will cease. If "OK" 36 is selected on the GUI of FIG. 7, the GUI of FIG. 8 will appear. The medical professional will select "Yes" 11 if the system is to use the standard protocol stored internally.

In a particular embodiment of the subject invention, prior to acquiring test data for a particular test, the computer-implemented software will acquire data for a 10-second interval, displaying and indicating detected R-waves or QRS complexes (see FIG. 31). This process allows the operator to confirm the placement of lead system 12, and the sensitivity settings that appear in the GUI of FIG. 7. If the test data is not completely satisfactory to the operator, the steps represented in FIGS. 7, 8, 9, and 10 may be iterated to allow the medical professional to reposition the leads, if necessary, to provide for optimal sensing and signal amplitude. During data acquisition, a window depicting the data being acquired appears. An exemplary display of this graphical depiction of acquired signal 47 appears in FIG. 10. After the typical 10-second acquisition time, the GUI of FIG. 11 or FIG. 12 may appear. The GUI of FIG. 12 gives the operator the opportunity for another approximately 10-second data acquisition period. If software-detected problems occur during data acquisition, a GUI such as the one displayed in FIG. 11 may appear, notifying the operator of potential problems. These features give the operator more control over the testing procedure, and advantageously provide for error control.

Typically, in one preferred embodiment of the invention, an auditory beeping occurs with R-wave acquisition. If no R-wave beeping occurs or if poor signal amplitude is noted, adjustments in the leads may again be required, and sensing verification should be repeated via the GUI of FIG. 12.

In situations where the operator is not performing standard protocols, the system will allow the operator to interactively set the pulse position. FIG. 13 is a graphical depiction of pulse 59 on display area 39. Under these circumstances, the operator may use the cursor keys on the keyboard (not shown), coupled to computer 27 (not shown in FIG. 13), to position the pulse location using an average of the QRS complex signals received during sensing verification.

In one preferred embodiment, the final step in the performance of the test sequence function involves performing and recording the test. Prior to performing and recording the test, the software will represent the GUI prompt of FIG. 14. This will allow the operator to control the timing of the test to ensure that both patient 35 and the operator are ready to proceed.

When the "OK" 36 selection is made from the GUI of FIG. 14, the GUI of FIG. 15 is generated, graphically depicting the R-wave 34 in real time. If "Cancel" 30 is selected, the operator is returned to the previous screen. The system is configured to emit an audible beep synchronously with each R-wave sensed. As indicated on the GUI of FIG. 15, pressing any key of the computer keyboard will halt the performance test sequence. If a key is depressed during the test sequence, the GUI notification screen of FIG. 16 appears, notifying the operator what has occurred.

This invention anticipates that several other events may occur that would halt acquisition, and similar GUIs to the GUI depicted in FIG. 16 will report such termination of the test procedure. For example, if R-wave sensing is indicated at a rate greater than 180 beats per minute, the test will automatically be halted. Further, if the invention is having difficulty sensing the R-wave, or the R-wave is in any way irregular, the test will be halted. If the test is interrupted during the execution of a test sequence, the sequence may be restarted at the beginning of the interrupted test by selecting "Yes" 11 from the GUI notification screen of FIG. 17, which will be displayed after the test sequence is halted. Selecting "No" 17 from the GUI of FIG. 17 causes the system to return to the main menu screen of FIG. 4. If any of the remaining menu items in drop-down menu 48 are selected, a shortcut to a previously-described procedure is executed. If "Quit" 19 (see FIG. 5) from Testing drop-down menu 48 is selected, the software program is closed.

FIG. 18 shows the View drop-down menu 55 engaged. View drop-down menu 55 provides access to functions required to select viewing options for data acquired or loaded from disk. Each test performed by the subject of the invention records 3 channels of data. The placement of electrodes (see FIG. 2) allows these signals to record far-field ECG in roughly orthogonal directions. This advantageously provides for a data representation that defines the signal in three dimensions. Axes have been labeled X, Y, and Z. The X signal is recorded, for example, from left lead 1 to right lead 2, with left lead 1 being the positive direction. The Y signal may be recorded from neck lead 5 to leg lead 6, with neck lead 5 being the positive direction. The Z signal may be recorded from back lead 4 to sternum lead 3, with back lead 4 being the positive direction. Other configurations may be possible, depending upon the judgment and needs of the patient and operator. In addition to the three required signals, at least two additional signals are preferably calculated. The X, Y, and Z signals are combined to produce a magnitude and direction signal. A magnitude signal can be used to detect signal variation independent of direction. A direction signal can be used to detect signal variation independent of magnitude. The upper portion of View drop-down menu 55 contains selectable options for each of the signals X 100, Y 102, and Z 104. The options appear checked on the GUI when they are selected. These selections allow the medical professional to select which signals are displayed during certain viewing modes. The lower portion of the pull-down menu contains the viewing modes. Each mode allows the user to view the current data set in a different way. The viewing modes, as they appear on drop-down menu 55, are "View Full Resolution," 119, which displays the X, Y, and Z signals at high resolution on monitor 23; "View 2 Minute Screen" 123, which displays a selected signal compressed into two minutes per screen; and "View QRS Change" 125, which displays the selected signals with normal average, biased average, and difference depictions. Selection of "Vector Angle" 139 displays the angular velocity and direction change of the average signal. "Position Bias Pulse" 111 displays the average of the selected signals, along with an indicator of pulse position. This advantageously allows interactive positioning of stimulation by the medical professional performing the diagnostics.

"Signal Averaged ECG" 135 displays signal-averaged ECG information for normal, biased, and difference signals. Typically, in the application of signal-averaged ECG 135, of primary importance to the medical professional is the flat area immediately following the QRS complex, ST segment 133. ST Segment 133 is targeted because of its lack of signal in normal people (see FIG. 31). This lack of signal allows the recognition of the presence of very small-amplitude signals that can occur in people with conduction problems indicative of a susceptibility to arrhythmia or other cardiac tissue abnormality. Further, abnormal signals may also exist within the QRS and be masked by the higher-amplitude signal present there. Since this invention has the ability to perform comparative analysis between stimulated and non-stimulated beats, a much greater sensitivity may be achieved in areas where a higher natural signal is also present. Additionally, by examining various areas of the QRS complex, information regarding size and position of conduction alteration may also be evident.

If "Options" 128 menu selection is made from View drop-down menu 55, the GUI of FIG. 19 is displayed. "Option" 128, which is selectable by the GUI, is represented in FIG. 19. This function allows for better interpretation of the data accumulated. The "High-Pass Cutoff" option 60 of the GUI in FIG. 19 can be set to use a fast-fourier transform (FFT), to filter out frequencies lower than those indicated prior to averaging. A zero setting disables high-pass filtering altogether. Low-pass cutoff 94 uses an FFT to filter out frequencies higher than those indicated prior to averaging. A setting of 1,000 disables low-pass filtering. Advantageously, lead effective modeling (LEM) can be selected in the GUI represented in FIG. 19. If LEM box 96 is checked, in a preferred embodiment, a 20-millisecond model of the impulse artifact is constructed, based on the first four simulations. This model is subtracted from subsequent simulations to reduce artifact in the displayed information. Any voltage shifts created during stimulation are also modeled and removed. LEM and this correction algorithm greatly reduce artifact created by stimulation. A muscle response correction algorithm may also be implemented by the invention to advantageously correct for signal artifacts during stimulation and acquisition cycles. Using this technique stimulation is provided to the patient within an LEM time period between the T and P waves, at the beginning and periodically throughout the stimulation and acquisition process. Response to the stimulations is determined up to about 50 milliseconds for each stimulation. LEM is then created by combining the response of the stimulations during this period to generate a response signal, whereafter the signal is used to mathematically attribute noise generated by electrical artifact and muscle activity. Also GUI selectable is a "60-Hz Notch FFT Filtering" 86 option, which advantageously filters out frequencies at the 60-Hz rate prior to averaging. Accumulation Start time 88 and End time 89 can also be input on the GUI indicated in FIG. 19. Accumulation Start time 88 controls the starting range for the accumulated difference measurement on the average screen. The Accumulation End setting 89 controls the ending range for the accumulated difference on the average screen. An exemplary result of selecting "View Full Resolution" mode 119 is depicted in FIG. 20. Signal characteristics X 167, Y 173, and Z 177 are graphed independently. Again, status bar 37 indicates the various selected parameters previously discussed.

Individual QRS status may be determined from the GUI of FIG. 21. The various options in the QRS Status window 97 are as follows: if the status indicated is "Biased," that means that the QRS complex has a stimulation associated with it. If it is "Normal," the QRS does not have an associated stimulation. The parameter "Valid" in status window 97 means that the QRS has past selection criteria which is included in the averaging. If the LEM stimulation is indicated (not shown), this means that the QRS complex is used for LEM. If "low correlation" is indicated (not shown) in status window 97, the QRS complex was too low and, therefore, was not used in the averaging. If there is a "Bad Interval" indication (not shown), then the preceding or following interval changed by greater than 300 milliseconds. If a "high-rate" status indication is indicated (not shown), the pulse rate exceeded 180 beats per minute and the QRS complex was not used in the averaging. If "manual exclusion" is indicated (not shown), that means that the QRS complex was manually excluded by the operator. If "Bad pulse Positioning" is indicated (not shown), the pulse position exceeded the tolerance set by the medical professional or the default tolerance. Further, it is possible to manually include or exclude a particular QRS from the averaging statistics by using the "Include" 162 and "Exclude" 168 selection buttons on the GUI of FIG. 21. A previous QRS complex may be viewed by selecting the "prior QRS" button 142. The next QRS complex can be viewed by the selection of the "Next QRS" button 143.

An exemplary result of selecting "View 2 Minute Screen" 123 is depicted in FIG. 22. The 2 Minute Screen mode allows the medical professional to view a selected channel in an overview mode. In this mode, a two-minute portion of the selected channel 138 is displayed on display area 39. R-wave correlation points and stimulation points are indicated on the display area of FIG. 20. R-wave correlation points are longer, white indications (not shown) above the waveform. Stimulation points are red indications (now shown) below the waveform. Note that both Full Resolution 119 and View 2 Minute Screen 123 modes display the current start and end time for the displayed portion of the test on status bar 37 at the bottom of the relevant GUI. Advantageously, as the operator scrolls through the data, these values change to indicate the portion of data currently being displayed.

An exemplary result of selecting "View QRS Change" 125 mode is depicted in FIG. 23. In FIG. 23, the upper graph 61 shows the average of all nonbiased QRS complexes. The middle graph 65 shows the average of all biased or stimulated QRS complexes. The lower graph 67 is the difference graph that shows the difference between the normal and biased waveforms. Statistics identifying the accumulated area under each curve are displayed on the right. A double-end arrow 33 on the lower graph indicates the range over which the statistics were generated. The end points can be adjusted in the view options window. The Difference graph contains cumulative Difference results along the bottom of each 10-millisecond region, based on the magnitude signal. FIG. 24 depicts the Vector Angle GUI. Vector Angle mode displays angular information 151 not reflected in the magnitude signal. The Vector angle mode displays changes in the direction of the electrical signal, whereas the Magnitude mode displays changes in the amount of electrical signal.

When the Signal Averaged ECG menu selection is made from View drop-down menu 55, the GUI of FIG. 25 is displayed on computer screen 23. The various graphs represent the Signal Averaged information for the Normal 43 and Biased 44 QRS complexes, along with the Difference 45 between the two. Standard QRS, LAS 40 and RMS 40 calculations can be made. Noise threshold is displayed along with the standard deviation of the noise, as can be seen on the GUI of FIG. 25.

Another drop-down menu 46 is the Data drop-down menu 58. Data drop-down menu 58 provides access to functions required for loading previously acquired data from storage, such as a hard disk located in computer 27, or from removable storage, such as a Zip™ disk or other removable storage media. Configuration of protocol steps is also supported here, along with typical backup and restore functions.

FIG. 27 is a GUI depiction of an exemplary menu for stored data. The date 16 and time 20 of acquisition, the identification 38, name 32, age 53, gender 54, bias information 63, R-wave sensitivity, and valid count 71 are all identified for reference, as can be noted in the upper area 14 as depicted in FIG. 27. Selecting "Load From Internal Disk" option 126 from drop-down menu 58 reveals the GUI depicted in FIG. 28. The GUI of FIG. 28 depicts a variety of test data 57 that can be selected.

If "Load Protocol Step" 131 is selected from the drop-down menu, the GUI of FIG. 29 is displayed. This function loads an identified protocol step 69 into the current test configuration. The GUI dialog box allows the operator to identify the protocol step to load. Current patient information is not changed. To select a test configuration as a protocol step, the GUI of FIG. 30 is used. The protocol step is entered into "Select Protocol Step" window 158 of the GUI, and "OK" 36 is selected to save the step.

Selection of "Restore" 114 from Data drop-down menu 58 restores data from an external media, such as a Zip™ disk, back to the internal hard drive of computer 27. Further, using the "Export" 195 command, data can be exported to certain spreadsheet software programs.

The "Append To Stats" option 163 can be selected to append the statistics of the current configuration parameters to the file. Advantageously, this option allows all test data sets in the current drive and directory to be processed using the current processing parameters and appended to the selected text, or .TXT, file. This useful option allows for batch processing and results based on altered settings.

Another menu 46 is Help drop-down menu 60. Full index and search capabilities of Help information is available. Further, on-line help, such as information gatherable through the Internet, is also anticipated.

A high-level operator flow chart for the software described above appears in FIG. 43. A typical embodiment of the method of using the software begins at the Attach Leads To Patient stage 280. As described above, the operator will then Invoke Testing 282 and Input Patient Information 284. If only a single test is desired, path 287 is taken, wherein the operator has a chance to Define Test Parameters 291. Otherwise, the operator has the choice of selecting All Tests Desired 289 and proceeding directly to Verify Sensing 293. If Verify Sensing 293 is Bad 295, then the lead positioning can be adjusted 297, and the verified sensing retried 294. Once the sensing is Good 198, the test parameters are loaded and the test is performed 288. Once the test is completed 292, there is a chance for the operator to see if more tests need to be performed 296. If "Yes" 290, then the next predefined tests are loaded 286, and the operator is returned to Test Parameters Loaded and Test is Performed 288. If no further tests are to be formed at the 296 state, the "No" path 299 is selected and the test is completed and leads are disconnected 300.

FIG. 44 is a depiction of the test control and data acquisition software flow chart. Raw data received from lead system 12 is received at the Realtime Test Control and Monitor Software 310, along with Realtime R-Wave Indicators 306. Realtime Test Control and Monitor Software 310 then controls and relays this information to generate GUIs to make a realtime display 312 on monitor 23. Inputs from the control system can control other test features, as well, such as User Abort Control 304 and the user's ability to perform Test Configuration 308. Realtime Test Control and Monitor Software 310 can also send the Raw Data 303 to storage 313, and save Subject & Test Information 315.

FIG. 45 depicts the software flow charts of the post-processing software. Annotation and post-processing control 332 controls View Options 325 as described above, and subject and test information retrieval from storage 320. Raw data from storage 326 is retrieved and analyzed for R-wave detection 332. If LEM generation 330 is requested, then LEM Correction 334 will be performed, and Correlated QRS Alignment 336 performed. Then, one to typically four processing options may be selected. Average Processing 340 can be selected for the data to be analyzed after being filtered through filtering process 338. Then the options of displaying 350 or saving 355 the data are available. If variance processing 342 is selected, the results may be displayed 350 or saved 355. Similarly, if Power Spectrum Processing 344 is selected, the results may be displayed 350 and/or saved 355. Also, Direction Vector Processing 346 may be selected and, again, the resulting information can be displayed 350 and/or saved 355.

FIG. 46 displays the lower-level flow diagram, more particularly, the stimulation timing software and the switch, shunt, relay, and stimulation control features that allow for efficient subpacing stimulation signals to be timely and efficiently administered, as well as to facilitate the ability of the invention to make fast recovery to prepare for the next QRS complex event. Raw Data Stream 370 is filtered by Filters 368 and is sent to Realtime LEM Generator 360, and any realtime LEM correction is made at 366. Realtime R-wave detection is determined at step 364; and, if detected, the realtime r-wave indications are passed on at 362. Realtime R-Wave Detection 364 is also linked with the Stimulation Timing Software 352 that determines the timing of the subpacing electrical pulse. Stimulation Timing Software 352 interacts with the switch on the relay and the stimulation control portion of the software 358. The computer interconnects to the electronic interface as shown at 372.

FIG. 36 depicts an exemplary series of QRS complexes 130, or R-wave events. As can be seen, interval 144 is defined by that interval from the beginning of one QRS complex to the beginning of the next QRS complex. During the testing provided by this invention, a Pulse-Delivery Point 110 is determined by the invention, and a subpacing current is delivered, typically as shown in FIG. 36. There is then the anticipated R-wave 115, based upon two previous R-waves. In one preferred embodiment, the response to the stimulation is determined for a period of up to about 50 ms after the stimulation. Any change in the characteristics of the QRS complex 130 following delivery of the subpacing pulse at delivery point 110 can be used in the diagnosis of a patient's susceptibility for arrythmia and cardiac tissue abnormality. A desired pulse position with respect to a detected R-wave is configured by the operator. When the intended position and time with respect to a detected R-wave is at or following the R-wave, then the device delivers a pulse after an appropriate-length delay following the most recently detected R-wave. When the intended position and time with respect to a detected R-wave are before the R-wave, then the device uses the previous R-interval 144 to determine an estimated time for delay by subtracting the desired amount from the R to R interval 144. The device then delivers the pulse after the determined delay following the most recently detected R-wave. The computer software is controlled with simulation and data acquisition during testing. During each test, the software delivers stimulation to alternating QRS complexes, based on realtime R-wave detection. Signals are recorded from lead system 12, along with the stimulation and R-wave detection locations. This is monitored and is terminated when the appropriate number of pulses have been delivered in the region identified in the test parameters.

Another process for arrythmia detection is that of t-wave alteman analysis. This process involves looking for alternations from beat to beat in the signal produced during the t-wave portion of the heart signal. The t-wave is the portion of the heart signal that follows the QRS "contraction" (see FIG. 31) of the heart. The QRS area is called depolarization. The t-wave is called repolarization because the cells are electrically preparing for the next depolarization. T-wave analysis involves computing the 'power' of each t-wave and looking for alternations in this power from beat to beat. This phenomenon tends to increase in people prone to arrhythmia. The use of t-wave alternan analysis with the previously-described technique of subthreshold stimulation is anticipated by this invention.

An overview of the operation of this invention can be seen in FIG. 33. Sensing Leads 202 pass received Signals 248 to the fast-recovery amplifier, at which time the Signals 248 are passed to the Analog to Digital converter 208. Thereafter, Data 250 is used to determine R-wave Detection 237 and for LEM modeling 215. Data 250 is also capable of going to Storage 218, and is further used for Post-Processing 240, where data 250 is eventually displayed to computer monitor 23. During the fast-recovery amplifier stage 254, Blanking Control 212, through Control 253, is used to compensate for blanking. This blanking control is initiated through the Software and Hardware Control Logic 234 via Control 253. Control 259 controls the R-wave detection 235 as it is passed to the Software and Hardware Control Logic 234. Software and Hardware Control Logic 234 further controls a Shunt Control 225 via Control 254; and Control 257 controls Current Controlled Driver 221. Hardware and Software Control Logic 234 passes Data 250 to the Digital to Analog Conversion 228, thereafter passing those Signals 255 to the Current Controlled Driver 221. At the appropriate time, Signal 255 is delivered to Stimulation Leads 206. Post-Processing 240 also performs LEM modeling 215, Digital Filtering 243, and Statistical Calculations 246, described in more detail below.

A significant part of the subject invention is the amplifier and driver circuitry located in electronic interface 18. Electronic interface 18 provides amplification of signals received from lead system 12 and amplifies those signals to a level of impedance readable by the computerized data acquisition/control system, such as computer 27. Electronic interface 18 also takes control signals from the computerized data acquisition/control system, such as computer 27, and provides stimulation into lead system 12, as described above. The amplifier circuitry is designed to record lead signals that occur immediately following the injection of energy into the lead system. The recording typically occurs within only several milliseconds of the injection of energy. Fast recovery is important to the system because of the need to sense electrical information very shortly after a stimulation. In one preferred embodiment shown in FIG. 37, each vector X, Y, and Z has its own amplifier, X amplifier 155, Y amplifier 165, and Z amplifier 175. Stimulator 180 controls subpacing pulse delivery in conjunction with computer 27; and the software Power Conditioning Circuit 182 powers amplifiers 155, 165, and 175 supplying Stimulator 180 with subpacing current. FIG. 38 is a wire-level diagram of FIG. 37, illustrating this advantageous design.

To provide for such fast recovery, several methods are employed. The sensing leads are comprised of fast-recovery material, such as tin, sodium, silver and silver chloride, or other such material know to those skilled in the art, to facilitate rapid dissipation of any energy induced by the system. Further, electronics interface 18 uses a multistage amplification scheme as known to those persons skilled in the implementation of amplifiers, with improvements for fast recovery. FIG. 38 shows a wire-level block diagram of this embodiment of electronic interface 18. In one preferred embodiment, electronic switches are placed between amplification stages, which are used to decouple stages within the amplifier. The amplifier must be switched into its high-impedance mode, with appropriate time allowances for all electrical switching to be completed prior to the application of any energy to the stimulation leads. Similarly when switching back to normal impedance mode, appropriate timings must be used to ensure that all stimulation energy is completely terminated prior to lowering the amplifier impedance. This timing must account for any engaging or disengaging delay in both the amplifier and energy delivery circuits. When the amplifier is in its normal- or low-impedance mode, it has a capacity to store up charge in a very short period of time. Therefore, application of stimulation energy, however short, in this mode will greatly increase undesirable artifact. Therefore, timing is critical in decoupling the amplifier to reduce artifact. Advantageously, switch timing is software-controlled in one preferred embodiment of this invention. Other timing means are known to those skilled in the art. Filtering is implemented by this invention to filter the acquired signal to eliminate possible high frequency, switch-related artifacts.

An additional clamping circuit is also employed to aid in the reduced recovery time during stimulation. As can be seen in FIG. 39, an electronic track and hold switch 160 is placed between two stages of the amplifier. Track and hold switch 160 remains closed during stimulation, and in a preferred embodiment, a blanking period following stimulation. FIG. 39 is a block diagram/flow chart of the operation of the isolated fast-recovery EKG amplifier. Differential input signal 261 enters the Differential First Stage Amplifier Circuitry 264. Thereafter, it is controlled by Clamping Circuit 117. The signal is thereafter controlled by Clamping Circuit 117. The signal is then conditioned by Bandpass Gain Stage 267 and is regulated by Impedance Switching Track and Hold Circuitry 160. As depicted in FIG. 39, Switch Control 277 and Switch Isolation circuitry 275 control the timing of the signal. At the appropriate time, signals pass to Low Pass circuitry 269 and then to Final Gain Stage 271 and Isolation Stage 273. Finally, the amplified signal leaves the fast-recovery EKG amplifier as Amplified Signal 278.

FIG. 40 is a schematic of the fast-recovery EKG amplifier. FIG. 40 depicts the circuitry implementing the flow chart of FIG. 39. As can be seen, differential inputs 183 connect to the differential first-stage amplifier circuitry 187. The next stage is clamping circuitry 184, which is in electrical communication with the bandpass gain stage 185. Next are the switch-and-hold circuitry 181, low-pass filter stage 189, and final gain stage 188. Isolated circuitry 186 and switching circuitry 181 are also depicted in FIG. 40.

FIG. 32 is a block diagram of the switching circuit. A clamping circuit is also added within the preswitch stages. The clamping circuit is designed to engage when the input signal is greater than about plus or minus 5 mV. When switch 70 is closed, the circuit behaves as a typical amplifier, using the reference lead as a body surface reference point for amplification of the differential signal between the positive and negative leads. Advantageously, this reference point is utilized during periods of blanking of the input signals. The clamping circuit remains inactive for input signals of plus or minus 5 mV. This allows amplification of normal skin surface ECG signals. During stimulation, the switch electronically disengages the amplification stages from each other. While open, switch 70 itself provides a hold function that holds constant the signal level for all postswitch stages 74. Switch 70 also decouples the reference signal from the preswitch stage 77. This decoupling advantageously prevents the preswitch stage from accepting any transient energy present during stimulation. In addition to switch 70, clamping circuit 62 engages when the input signal of greater than plus or minus 5 mV occurs. This clamping circuit 62 uses reference lead 9 to measure a baseline. A baseline shift is caused by the remnant charge left in the patient's body following the stimulation, shunting and modeling cycles performed by a preferred embodiment of the invention. This remnant charge equalizes over time at an exponential rate referred to as baseline decay. Compensation for baseline effects can be done by subtracting a non-stimulated waveform from a stimulated wave form. Further, a baseline shift with a time constant decay may also be utilized. The decay rate may be modeled by sampling the decay rate over a predetermined interval, for example, about 10 ms. The decaying baseline shift can then be mathematically removed from the acquired data. Advantageously, the decaying baseline shift may be removed for predetermined intervals, for example, intervals up to about 300 ms. Baseline noise can advantageously be reduced by filtering and statistical noise reduction by this invention, Whenever the input signal deviates from this baseline by more than 5 mV, the internal amplification stage is held at that level. This further reduces the effect of transient voltages generated during stimulation. These two features work together to keep the amplifier stages as close as possible to their prestimulation values, advantageously providing a very fast recovery time. An additional circuit in postswitch stage 74 provides a filter that eliminates any possible high-frequency, switch-related artifact that may occur. This is required because of the nature of the switch employed. This recovery technique is incorporated within the amplifier in one preferred embodiment of this invention.

FIG. 41 is a flow chart/block diagram of the isolated driver section of the subject invention. This is additional circuitry located within electronic interface 18. This driver section depicted in FIG. 41 has the characteristics to shape the energy delivery pulse to reduce rise-and-fall slopes, thereby reducing induced artifact signals. Further, the isolated driver depicted in FIG. 41 provides for shunting of any charges built up as a result of energy delivery. Shunting means may include switching from a high-impedance path to a low-impedance path for a short period of time to dissipate unwanted voltage that is present. The switching between high and low impedances is designed to occur within a time of less than 1 ms. Typically, high impedance is greater than about 5,000 Ohms, and low impedance is less than about 500 Ohms. This shunting means can be connected between more than one energy delivery lead. Further, the driver employs a constant current circuit, thereby allowing control over energy delivery and varying lead or physiological impedances. As can be seen from FIG. 41, the Current Control 197 communicates with Isolated Driver Circuitry 193. Advantageously, there is also safety circuitry, which includes Safety Fuse 199 and Isolated Safety Relay 198, controlled by Safety Relay Control 192. Shunt Control 196 then controls the Isolated Shunt Circuitry 170, which timely delivers the subpacing current output 194 to the subject.

FIG. 42 is a schematic level of an exemplary isolated driver section. Blocked off on the schematic are Isolated Driver section 193, Safety Fuse 172, safety switch 174, and shunting circuitry 170.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations which fall within the spirit and broad scope of the invention.

BRIEF DESCRIPTIONS OF THE DRAWINGS

FIG. 1 depicts the broad overview of the invention, showing the patient electronic interface computer.

FIG. 2 is an exemplary depiction of a patient showing possible electrode patient locations.

FIG. 3 is a more close-up view of the lead system, showing the connector and attached electrodes.

FIG. 4 depicts the principal graphical user interface (GUI) generated by the computer and the software portion of the invention.

FIG. 27 is the "Accessing Stored Subject Data" GUI generated by the computer and software portion of the invention.

FIG. 28 is the "Open" GUI generated by the computer and software portion of the invention.

FIG. 29 is the "Protocol Steps" GUI generated by the computer and software portion of the invention.

FIG. 30 is the "Select Protocol Step" GUI generated by the computer and software portion of the invention.

FIG. 43 is a high-level flow chart of the operation of the software.

FIG. 44 is a lower-level flow chart of the test control and acquisition portion of the software.

Figure 5:
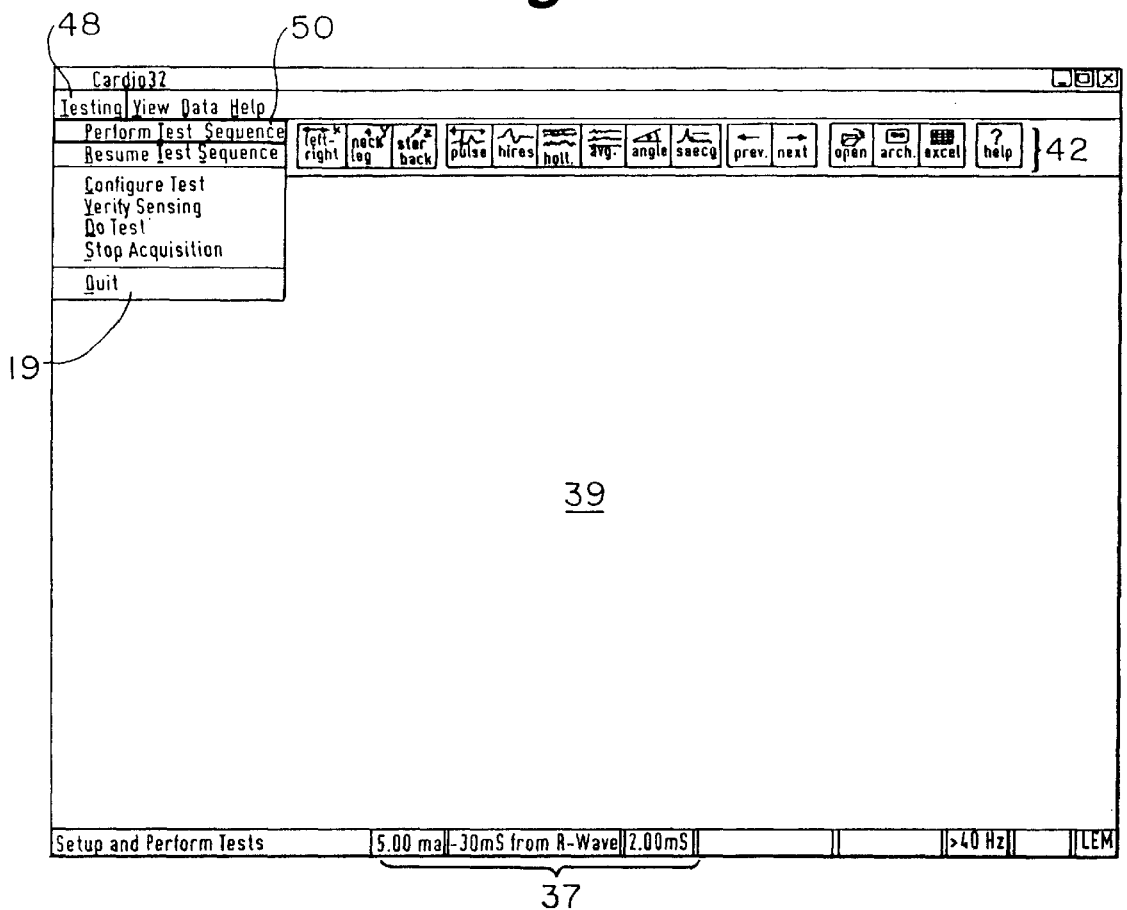
FIG. 5 is the principal GUI generated by the computer and software portion of the invention, with the testing menu engaged.
Figure 6:
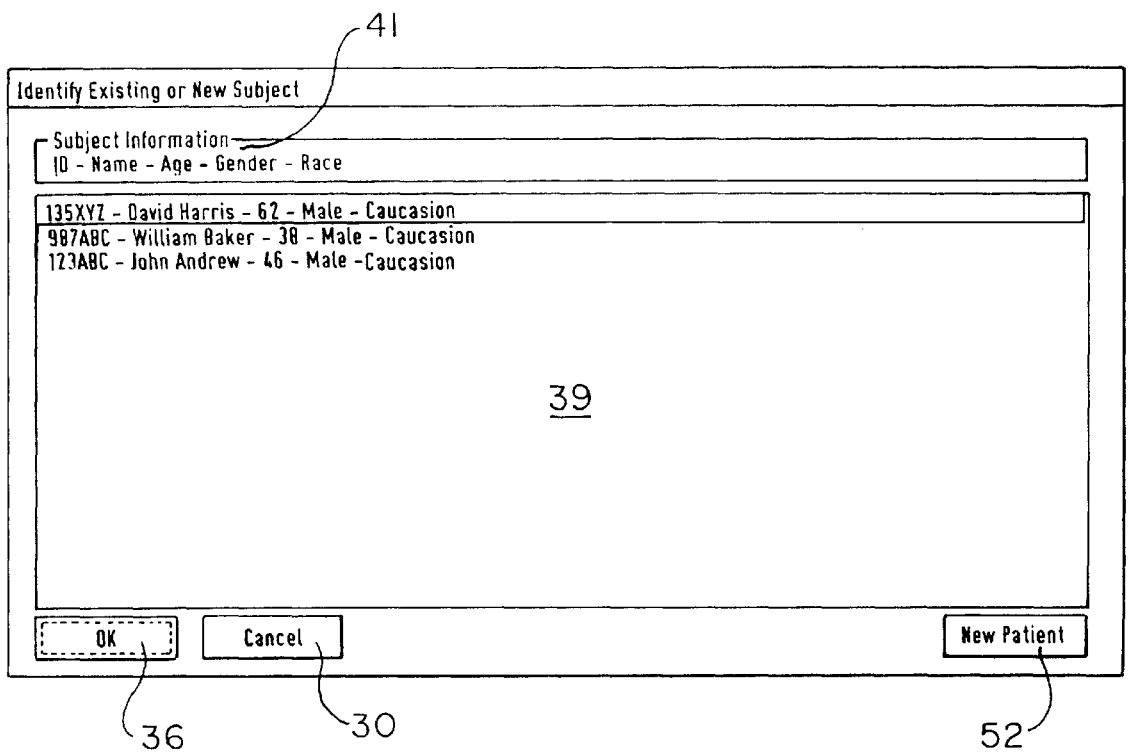
FIG. 6 is the "New Subject" GUI.
Figure 7:
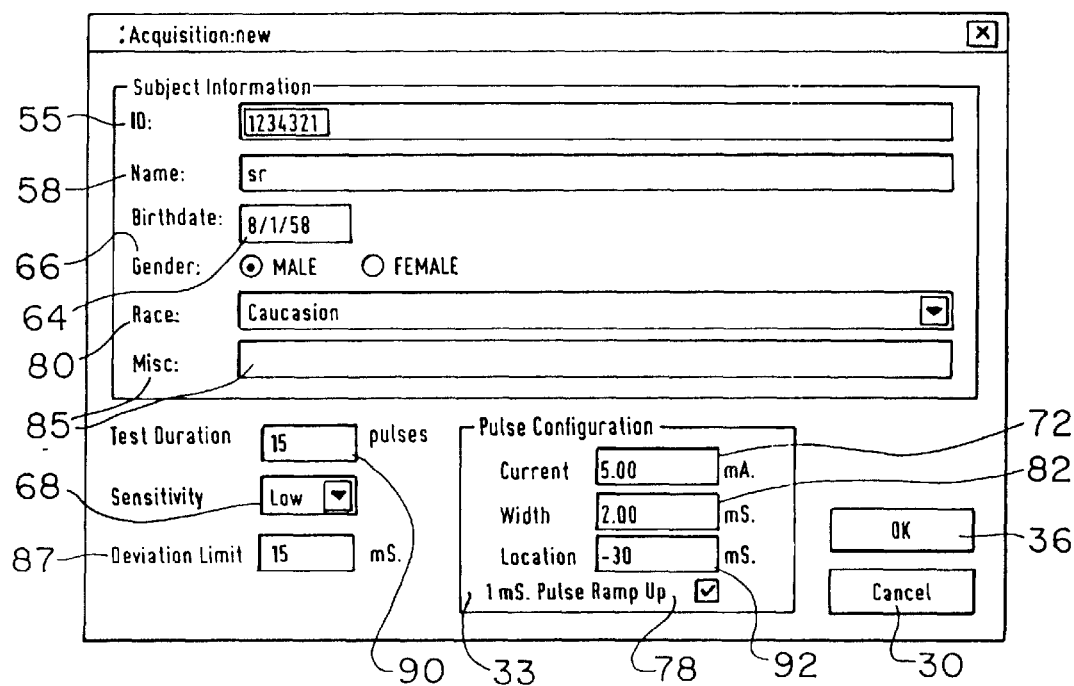
FIG. 7 is the "Acquisition" GUI.
Figure 8:
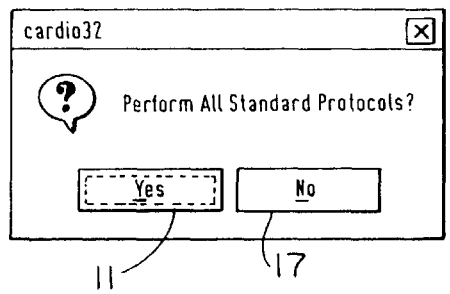
FIG. 8 is the "Perform All Standard Protocols" GUI.
Figure 9:
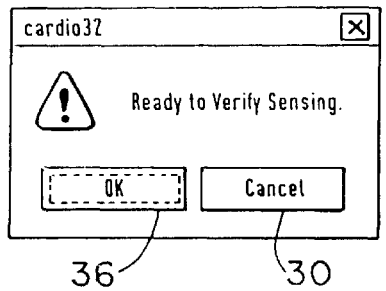
FIG. 9 is the "Ready to Verify Sensing" GUI.
Figure 10:
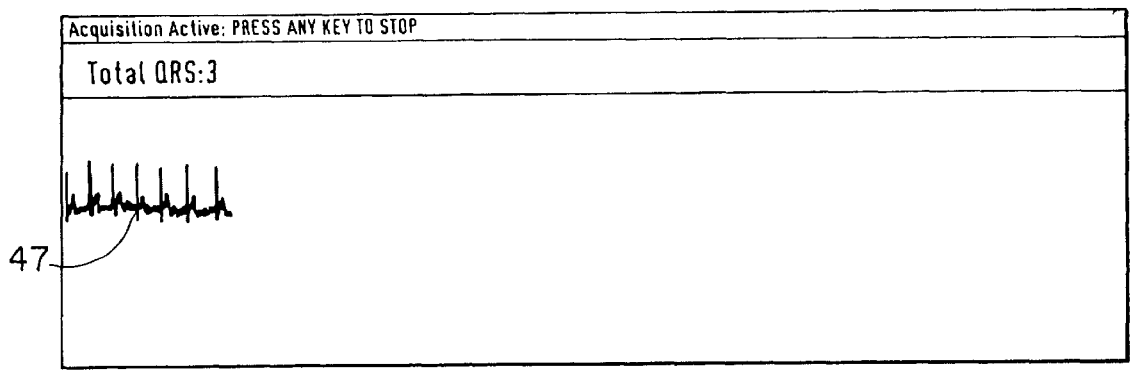
FIG. 10 is the "Acquisition Active" GUI generated by the computer and software portion of the invention.
Figure 11:
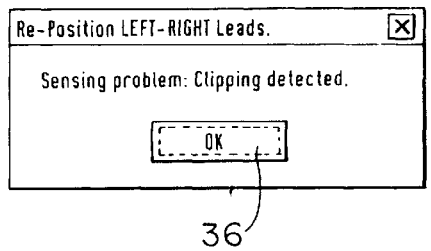
FIG. 11 is the "Sensing Problem" GUI generated by the computer and software portion of the invention.
Figure 12:
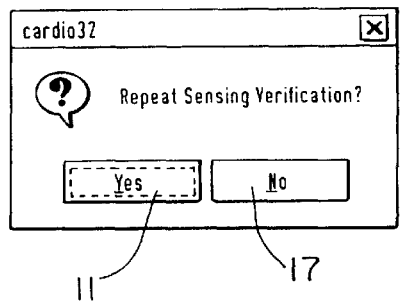
FIG. 12 is the "Repeat Sensing Verification" GUI generated by the computer and software portion of the invention.
Figure 13:
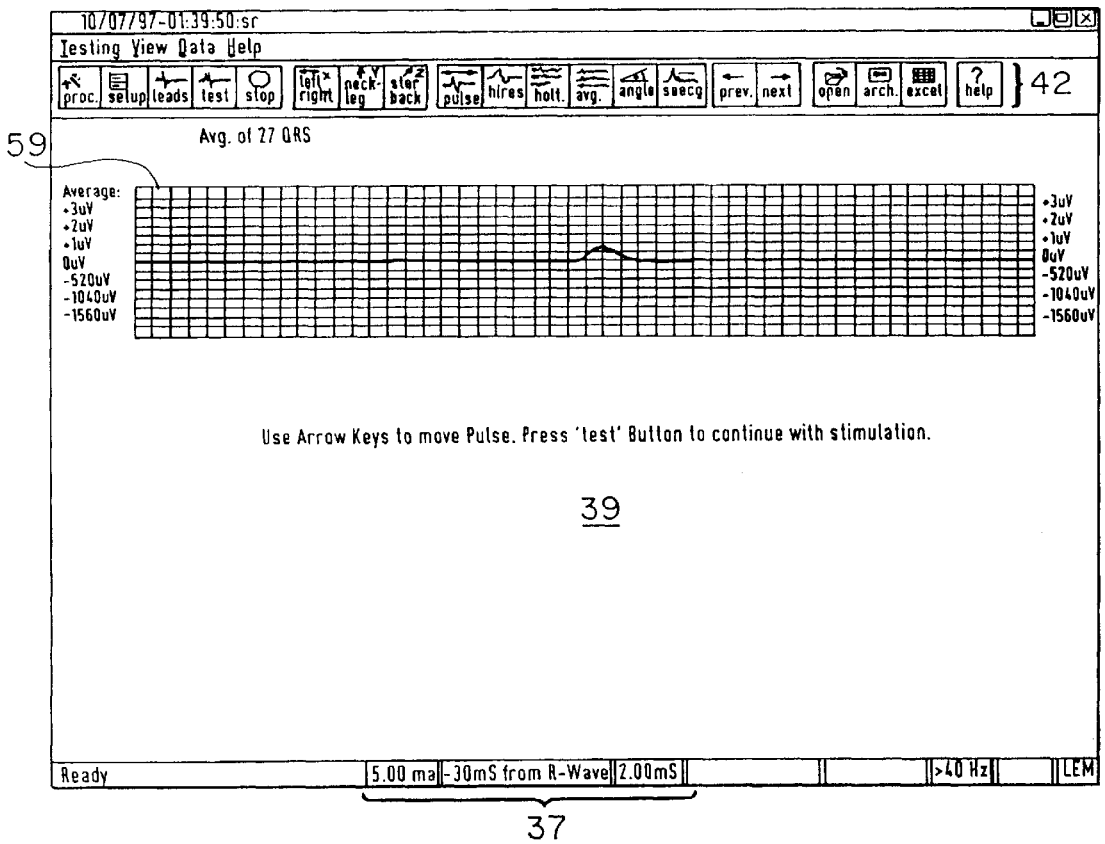
FIG. 13 is the principal GUI generated by the computer and software portion of the invention, depicting a pulse graph.
Figure 14:
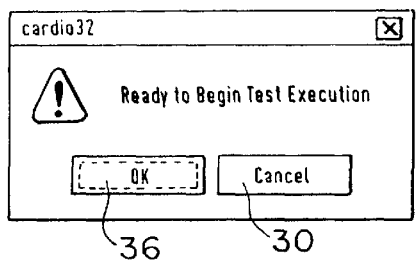
FIG. 14 is the "Ready to Begin Testing Execution" GUI generated by the computer and software portion of the invention.
Figure 15:
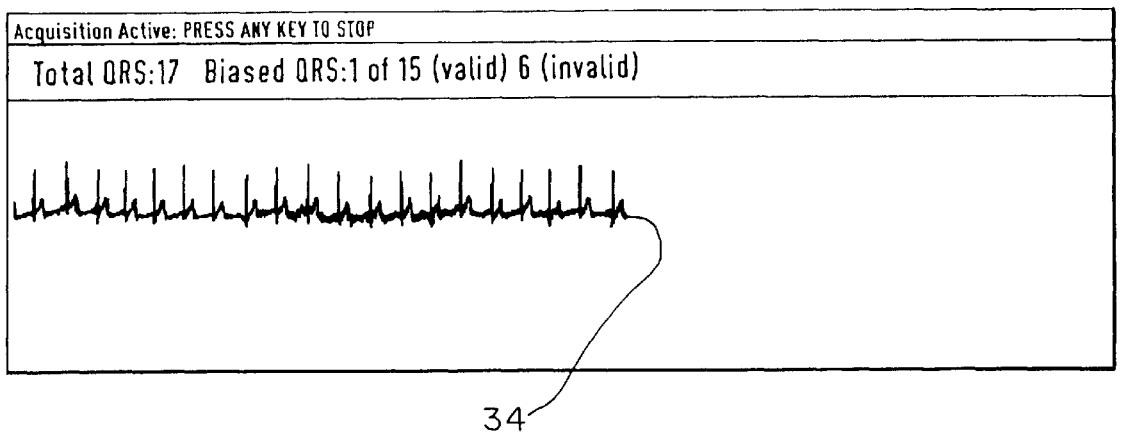
FIG. 15 is the "Acquisition Active" GUI generated by the computer and software portion of the invention, depicting realtime R-wave acquisition.
Figure 16:
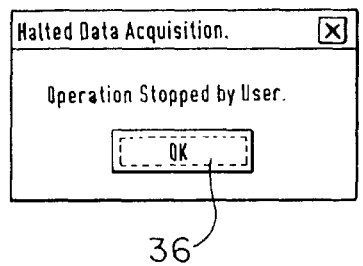
FIG. 16 is the "Halted Data Acquisition" GUI generated by the computer and software portion of the invention.
Figure 17:
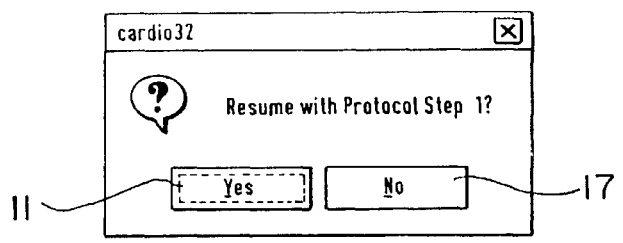
FIG. 17 is the "Resume with Protocol" GUI generated by the computer and software portion of the invention.
Figure 18:
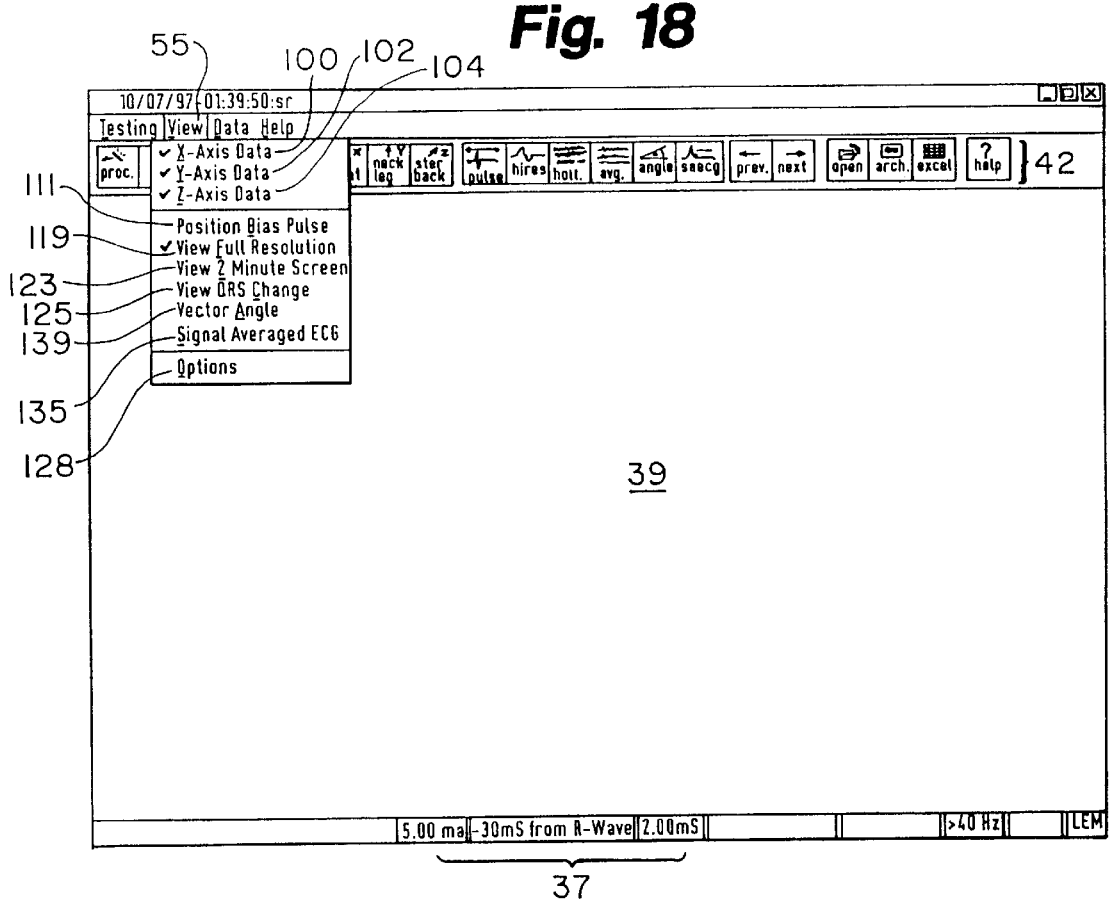
FIG. 18 is the principal GUI generated by the computer and software portion of the invention, depicting the "View" drop-down menu engaged.
Figure 19:
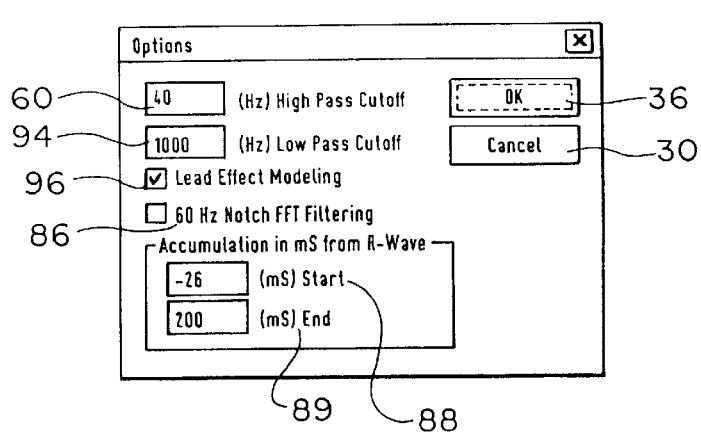
FIG. 19 is the "Options" GUI generated by the computer and software portion of the invention.
Figure 20:
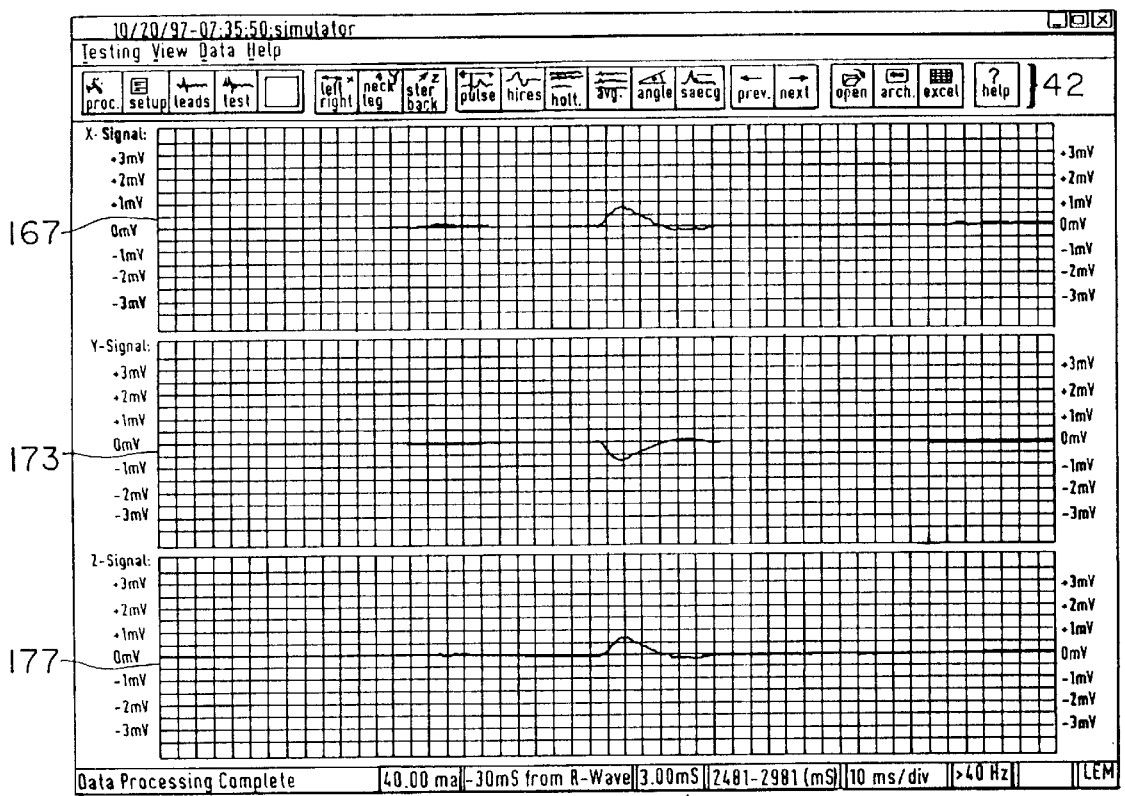
FIG. 20 is the "Simulator" GUI generated by the computer and software portion of the invention.
Figure 21:
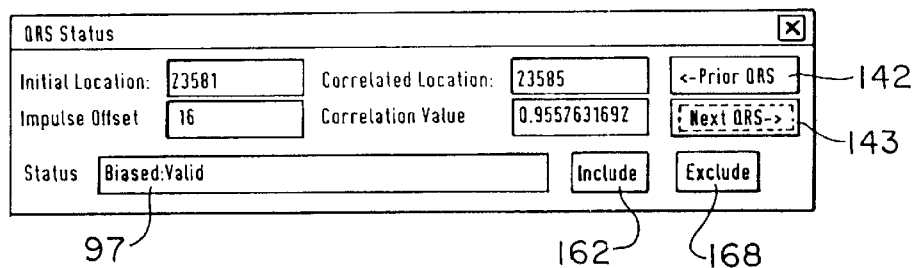
FIG. 21 is the "QRS Status" GUI generated by the computer and software portion of the invention.
Figure 22:
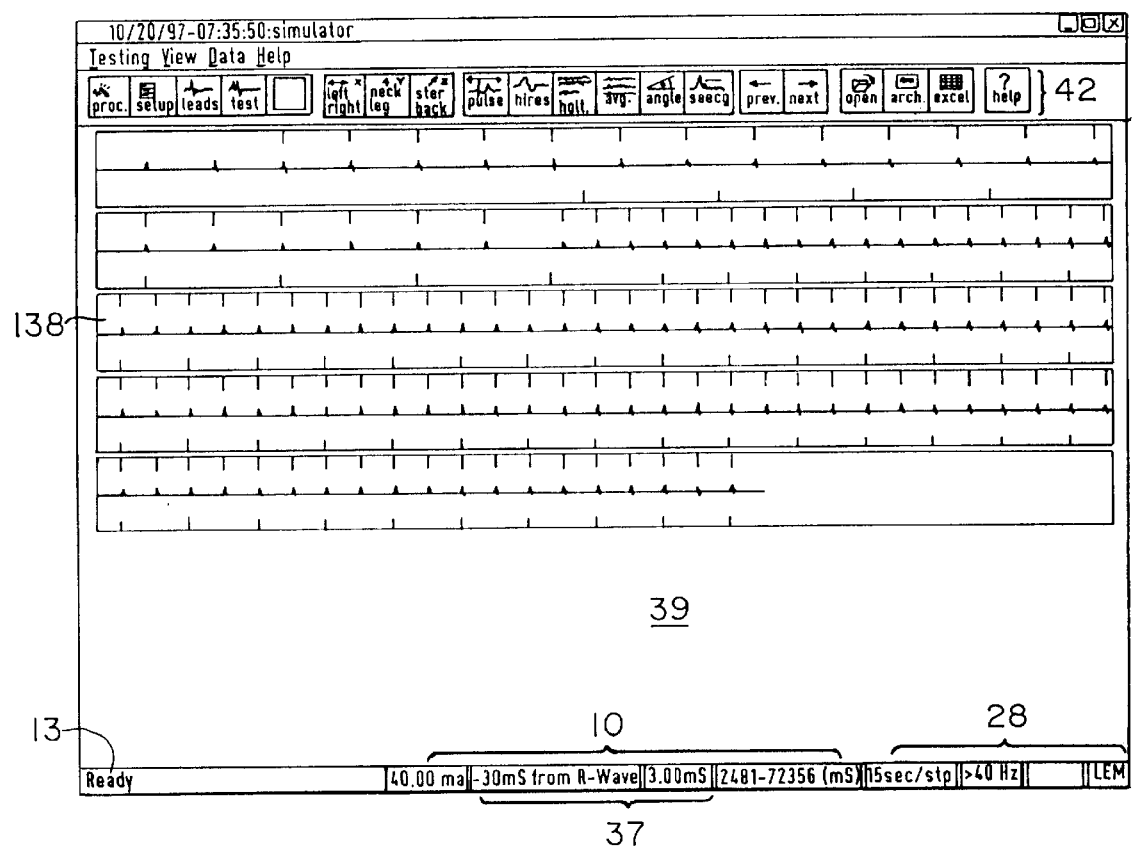
FIG. 22 is the "Simulator" GUI generated by the computer and software portion of the invention, depicting a further display option.
Figure 23:
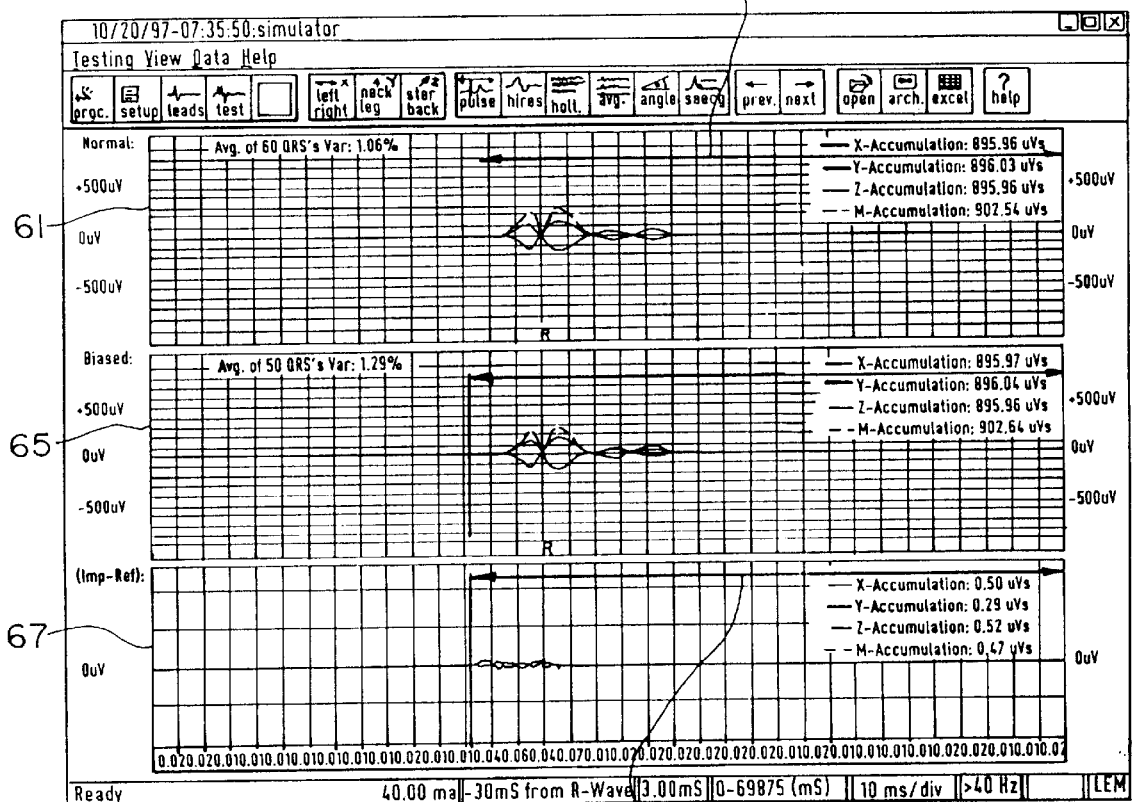
FIG. 23 is the "Simulator" GUI generated by the computer and software portion of the invention, depicting a further display option.
Figure 24:
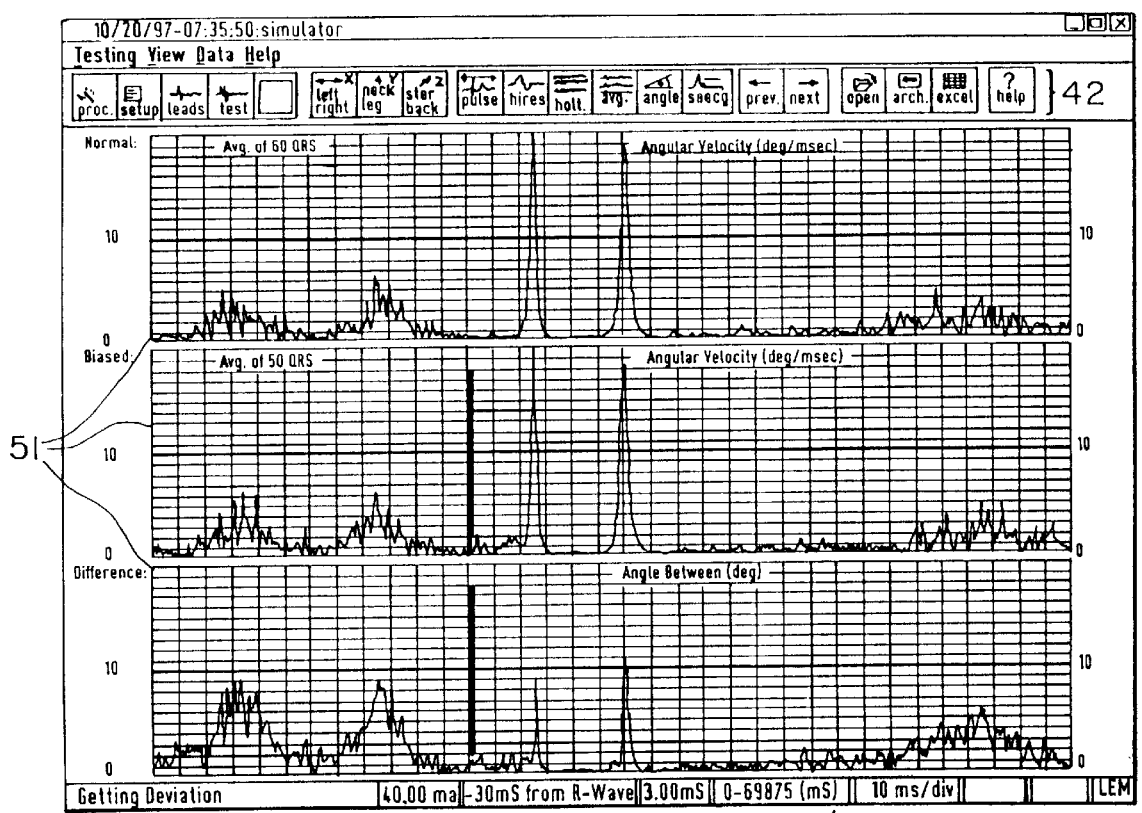
FIG. 24 is the "Simulator" GUI generated by the computer and software portion of the invention.
Figure 25:
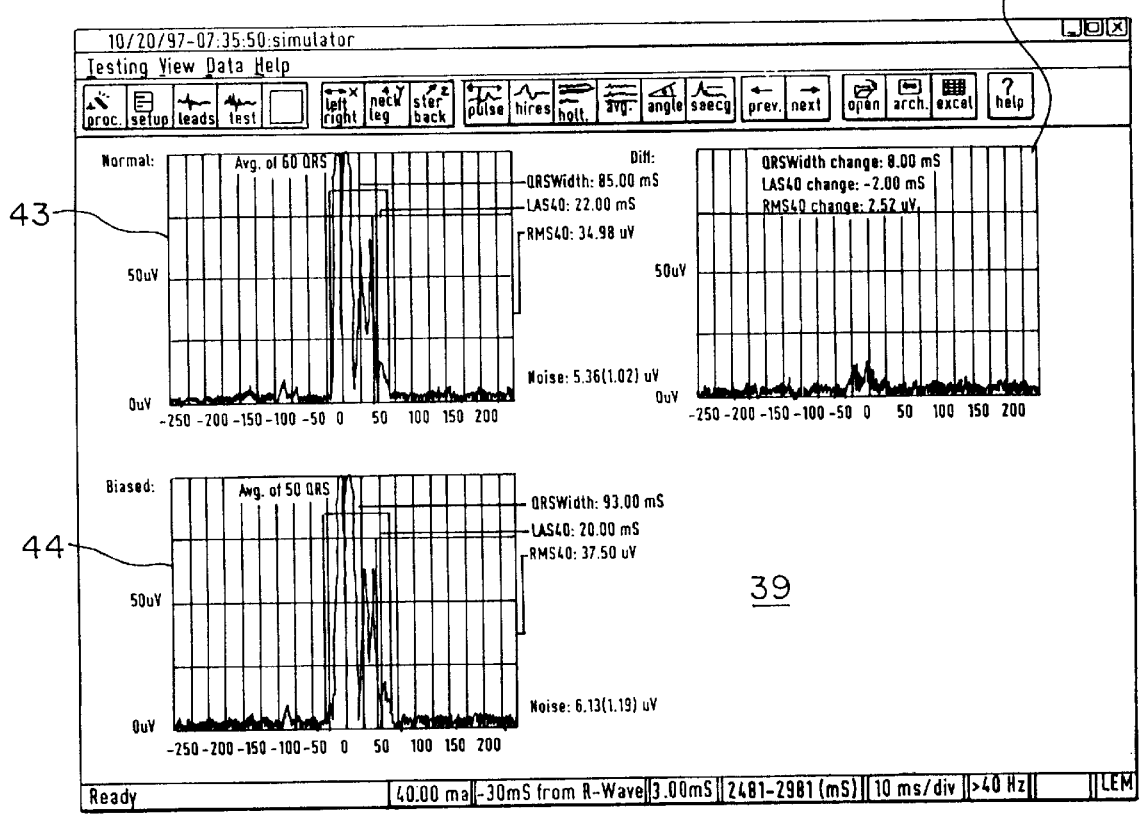
FIG. 25 is the "Simulator" GUI generated by the computer and software portion of the invention.
Figure 26:
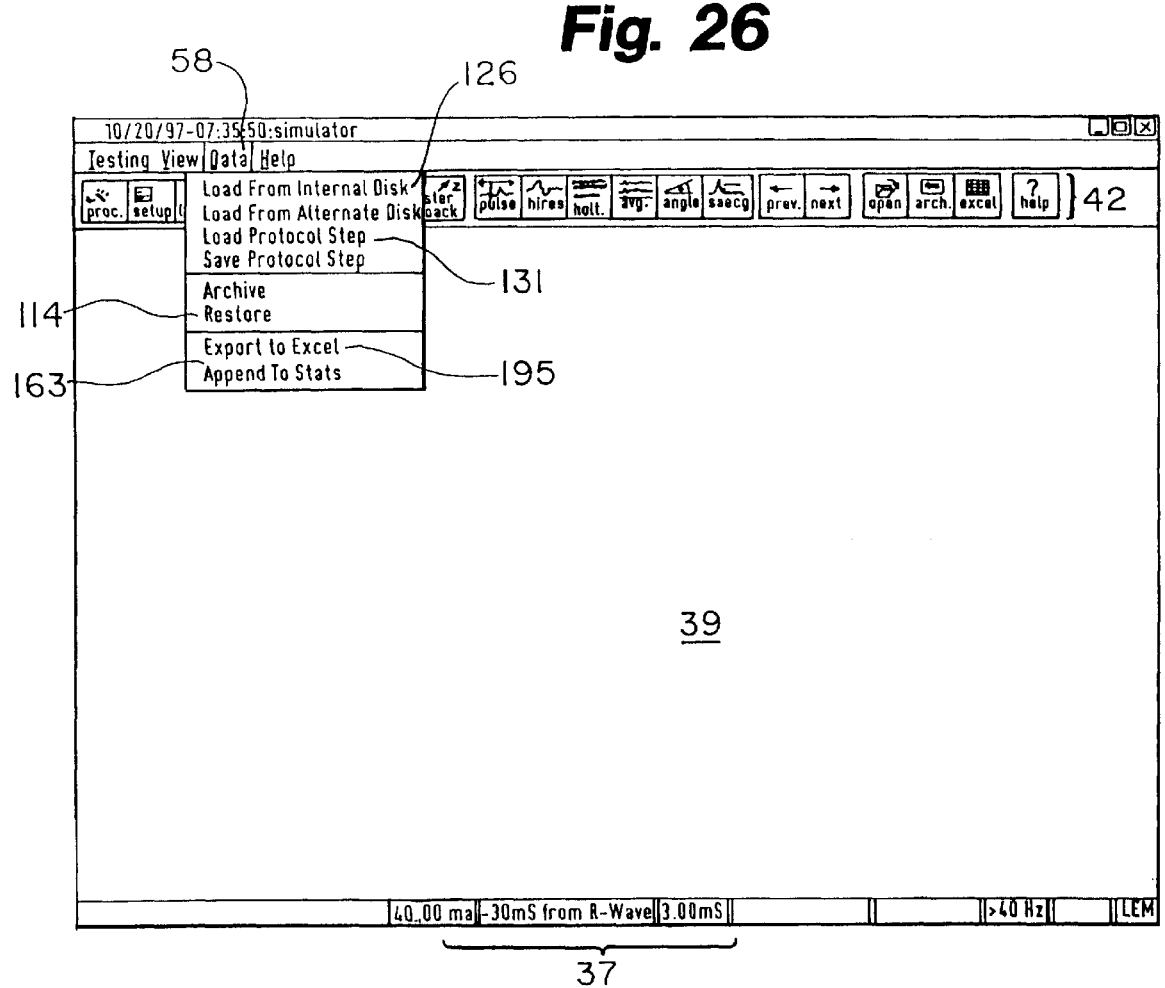
FIG. 26 is the principal GUI generated by the computer and software portion of the invention, depicting the "Data" drop-down menu engaged.
Figure 31:
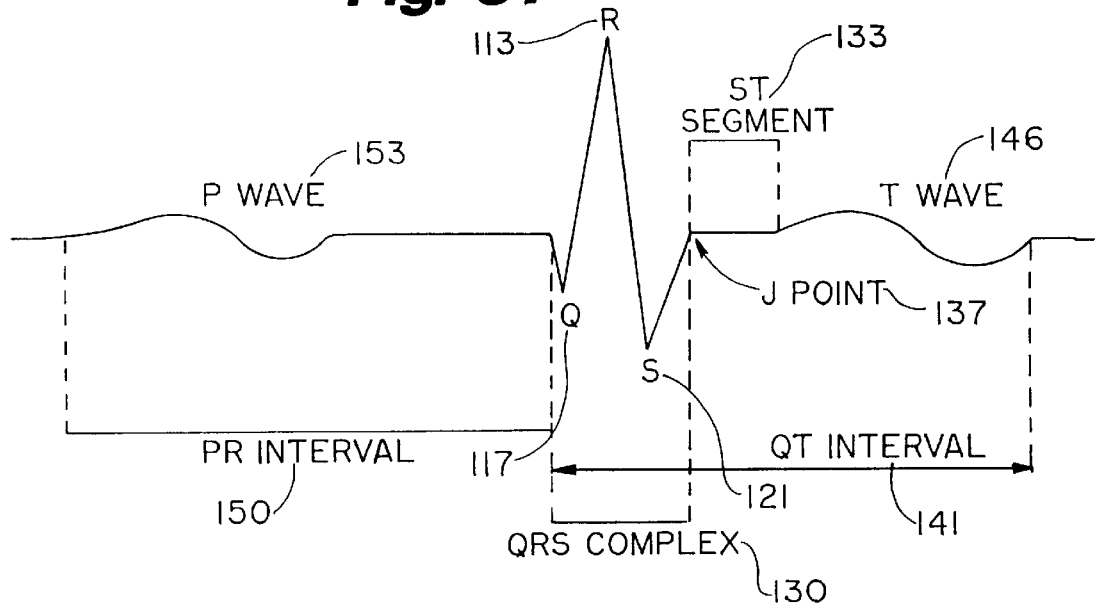
FIG. 31 is an exemplary EKG signal.
Figure 32:
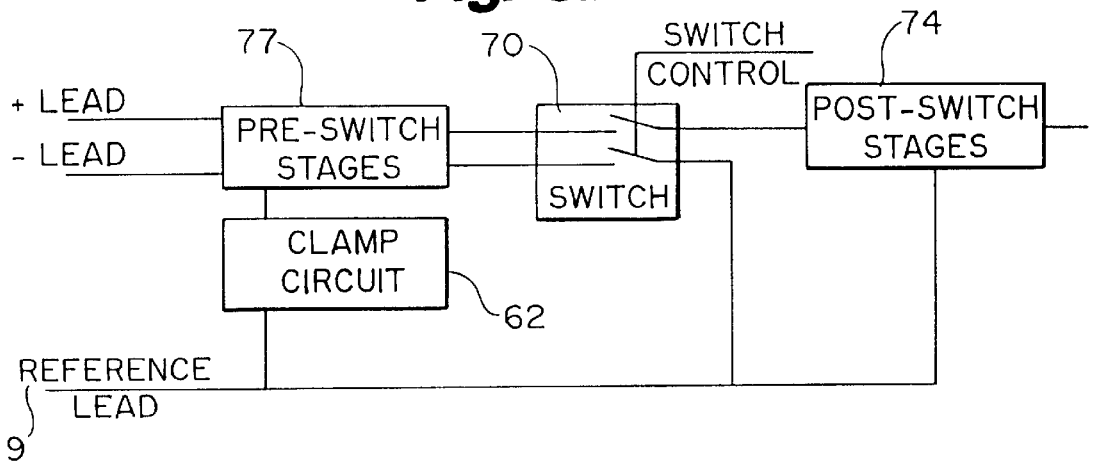
FIG. 32 is a block diagram of switching and planting circuit of the electronic interface.
Figure 33:
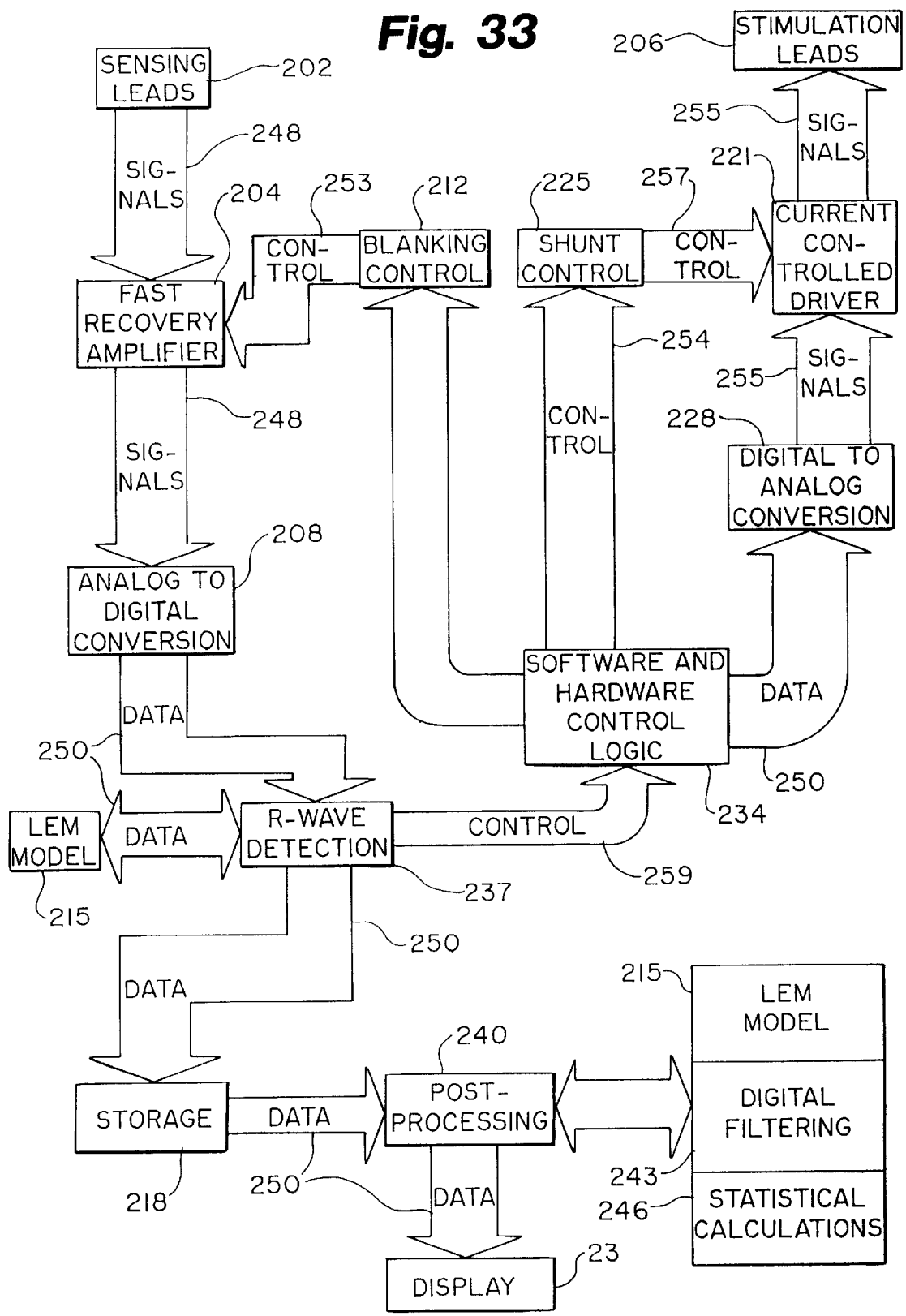
FIG. 33 is a flow chart showing the overall interaction of the invention.
Figure 34:
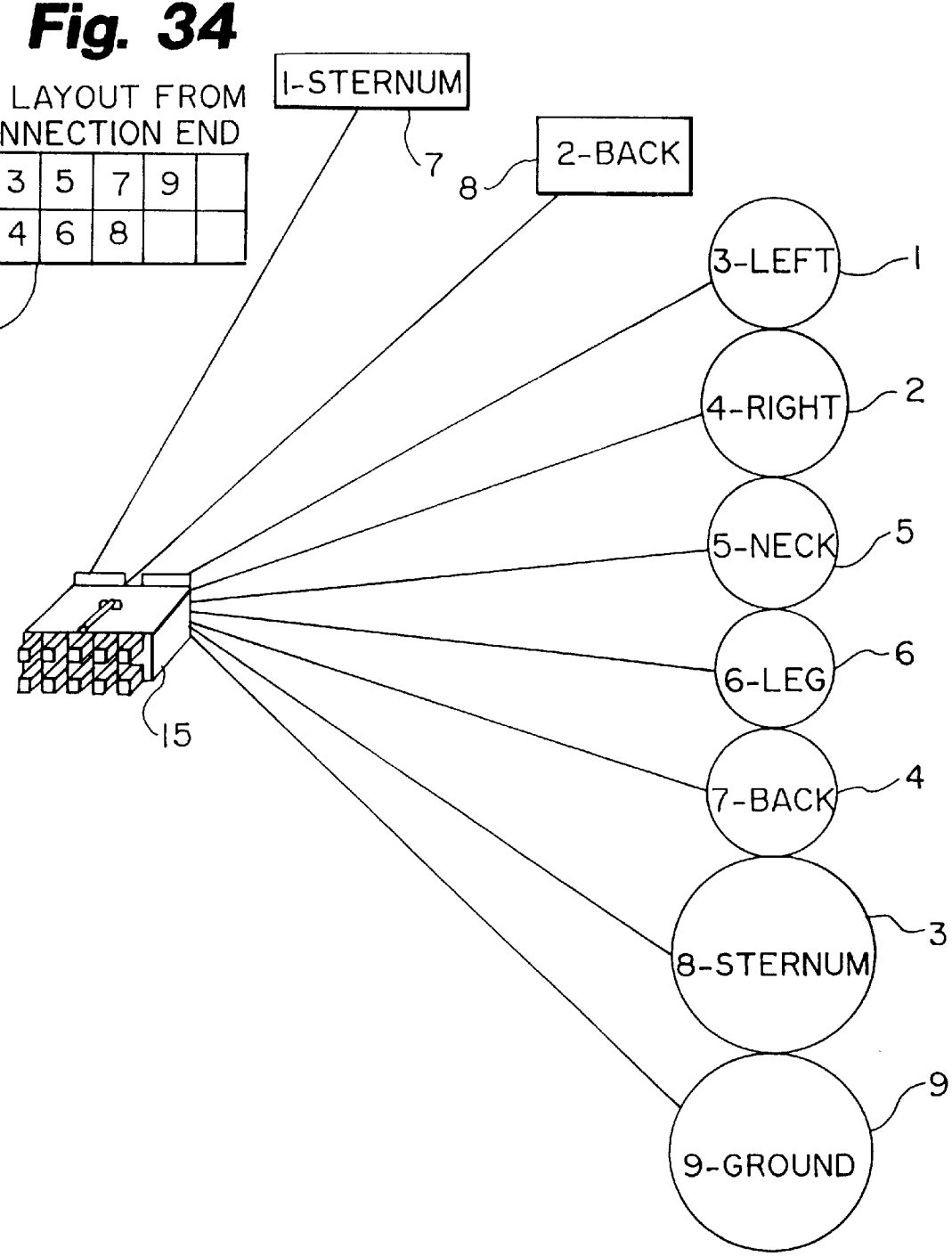
FIG. 34 is a more detailed view of the connector and attached leads, showing pin layout.
Figure 35:
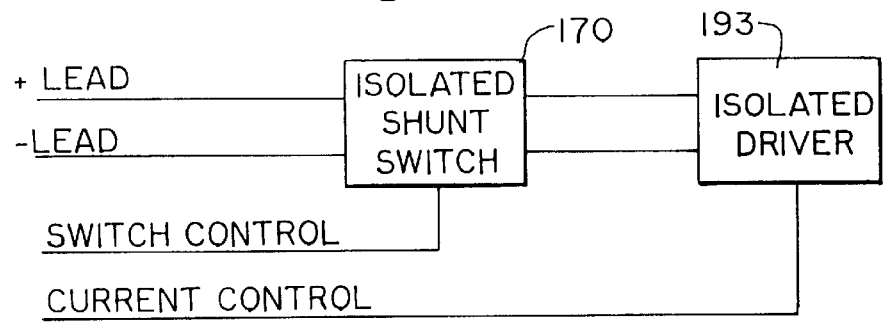
FIG. 35 is a block diagram of the isolated driver and shunting switch, a portion of the electronics interface.
Figure 36:
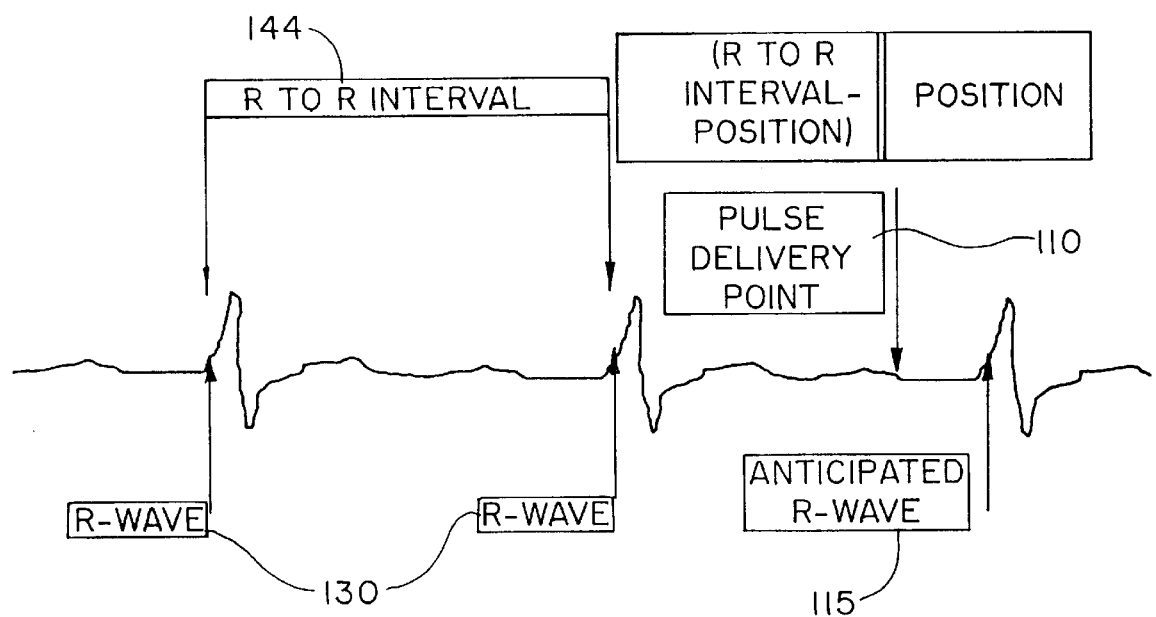
FIG. 36 is an exemplary series of QRS complexes.
Figure 37:
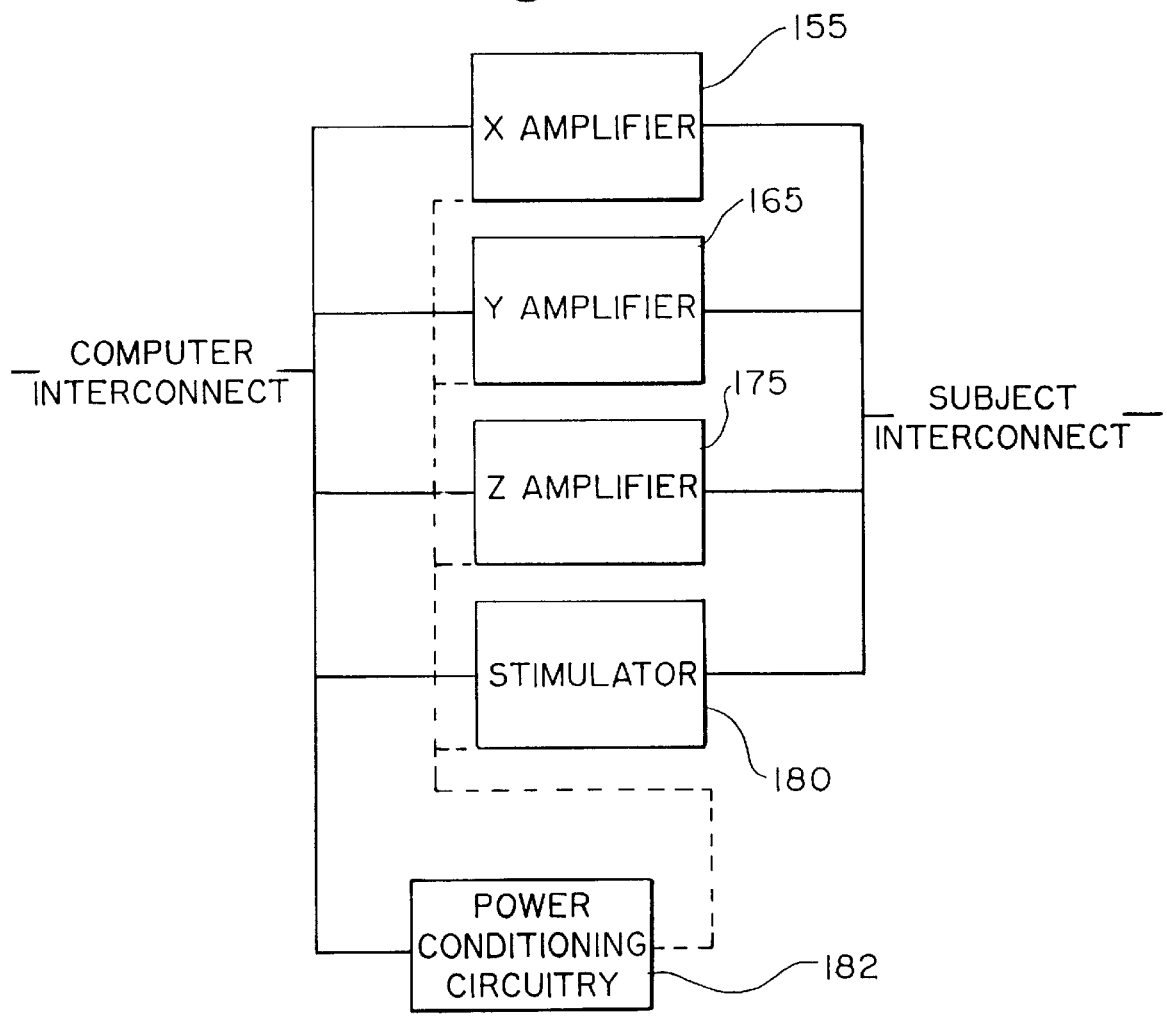
FIG. 37 is a high-level block diagram of the electronics interface.
Figure 38:
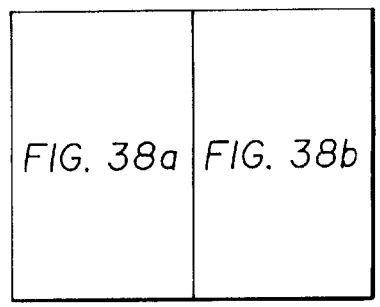
FIG. 38 is a wire-level depiction of the electronics interface.
Figure 38A:
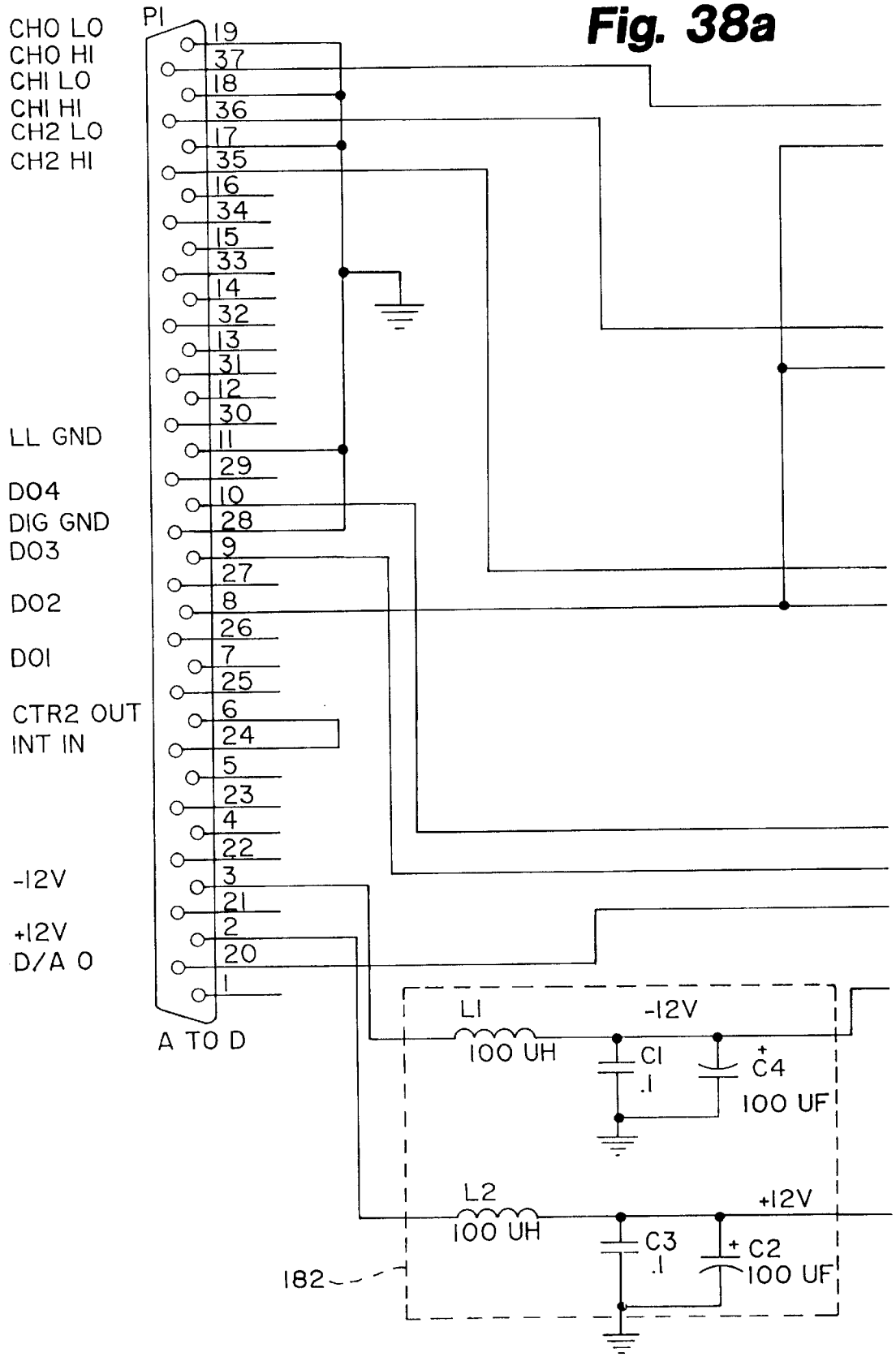
Figure 38B:
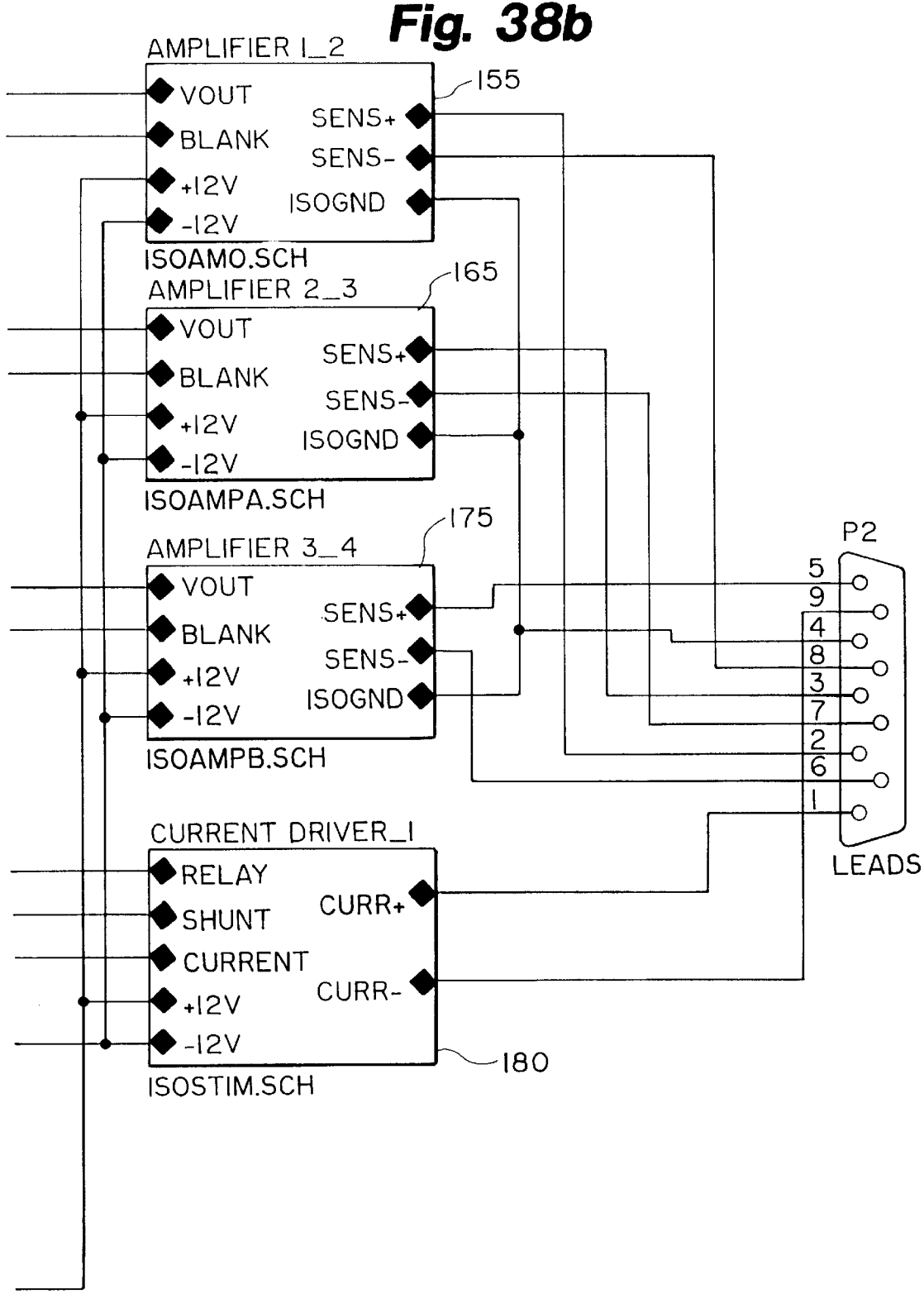
Figure 39:
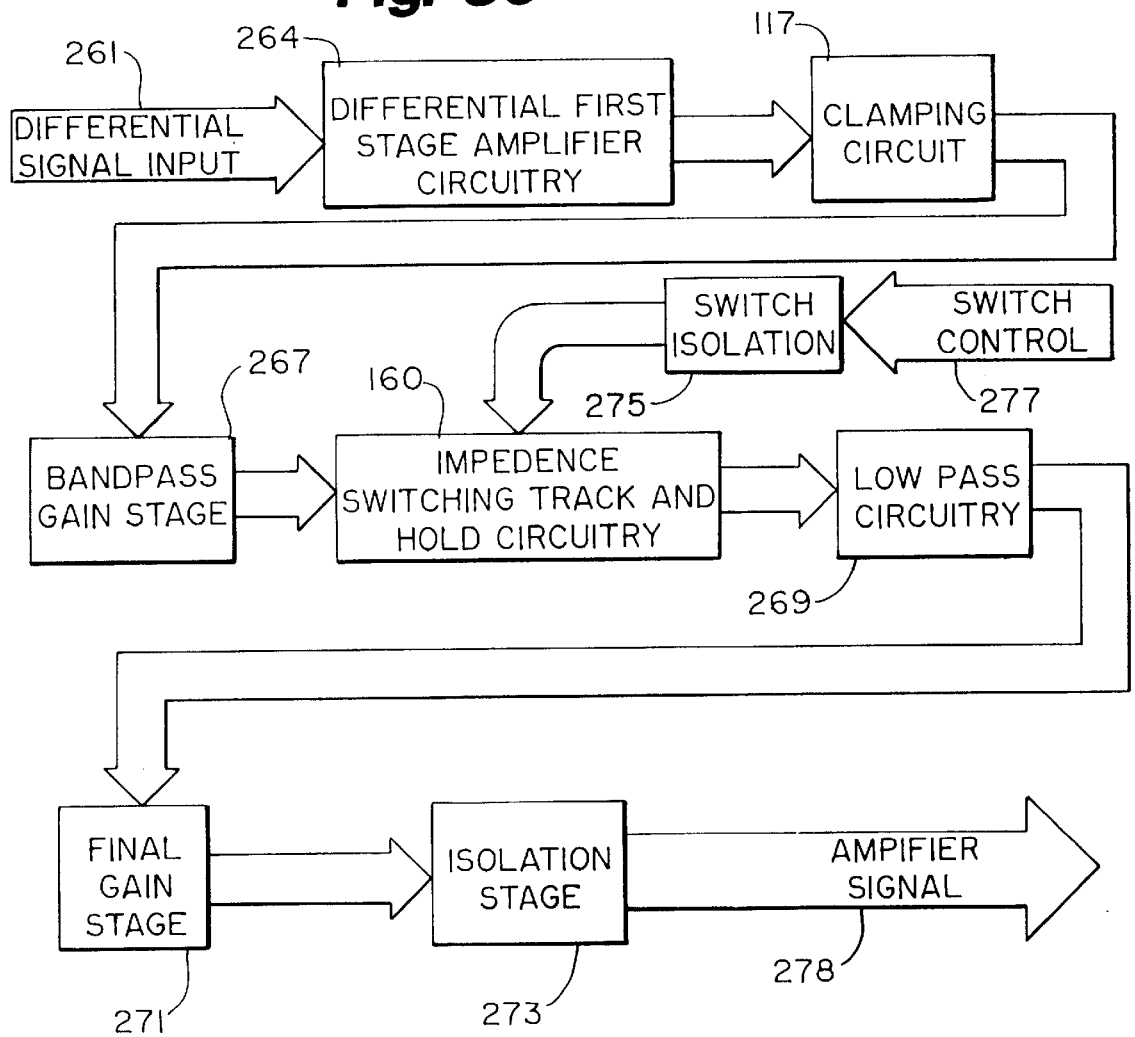
FIG. 39 is a flow chart/block diagram of the isolated fast recovery EKG amplifier.
Figure 40:
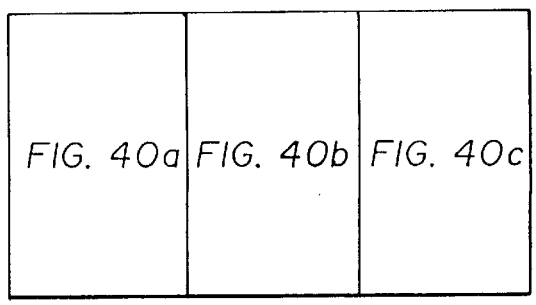
FIG. 40 is a schematic of the fast-recovery EKG amplifier.
Figure 40A:
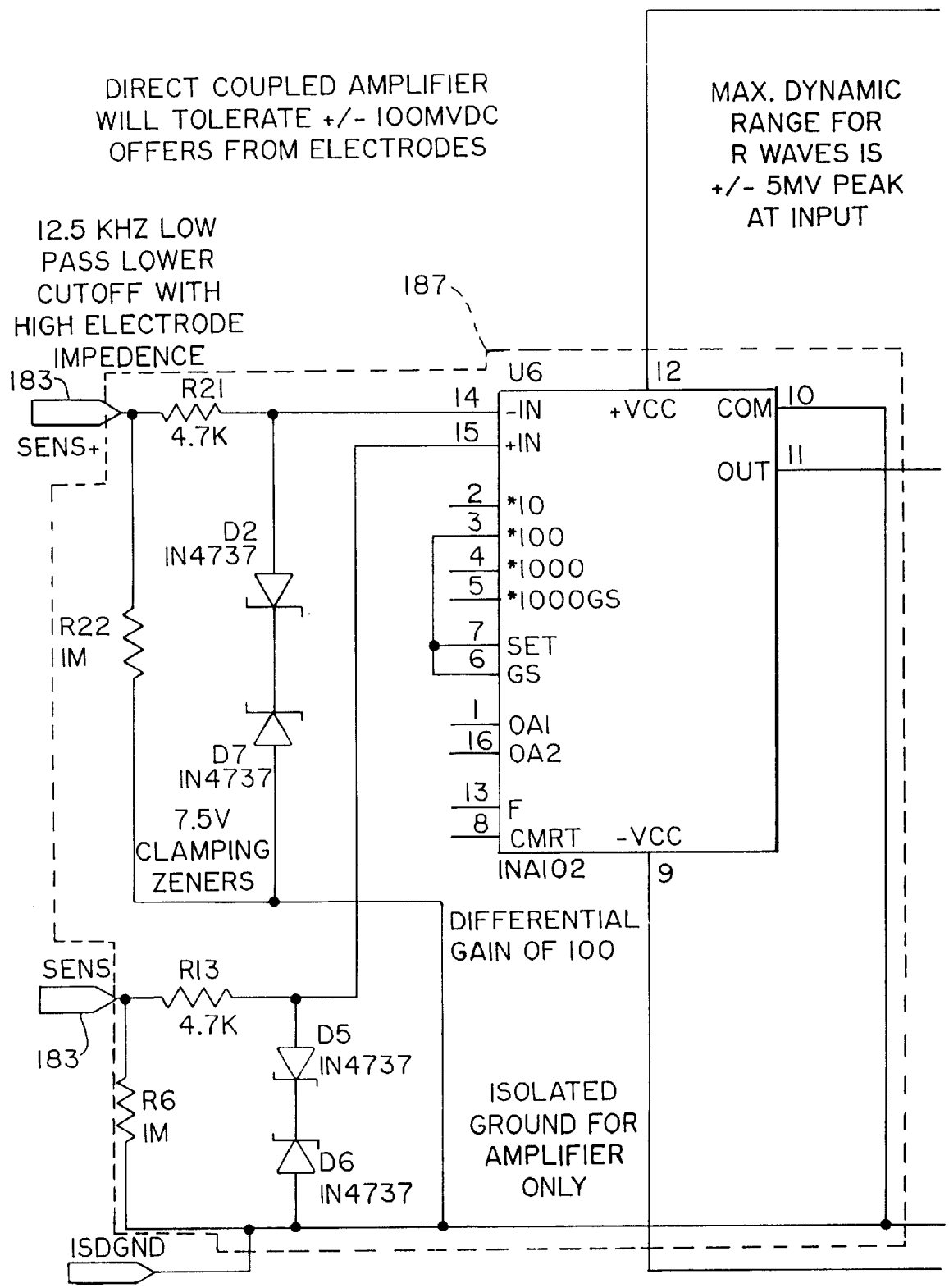
Figure 40B:
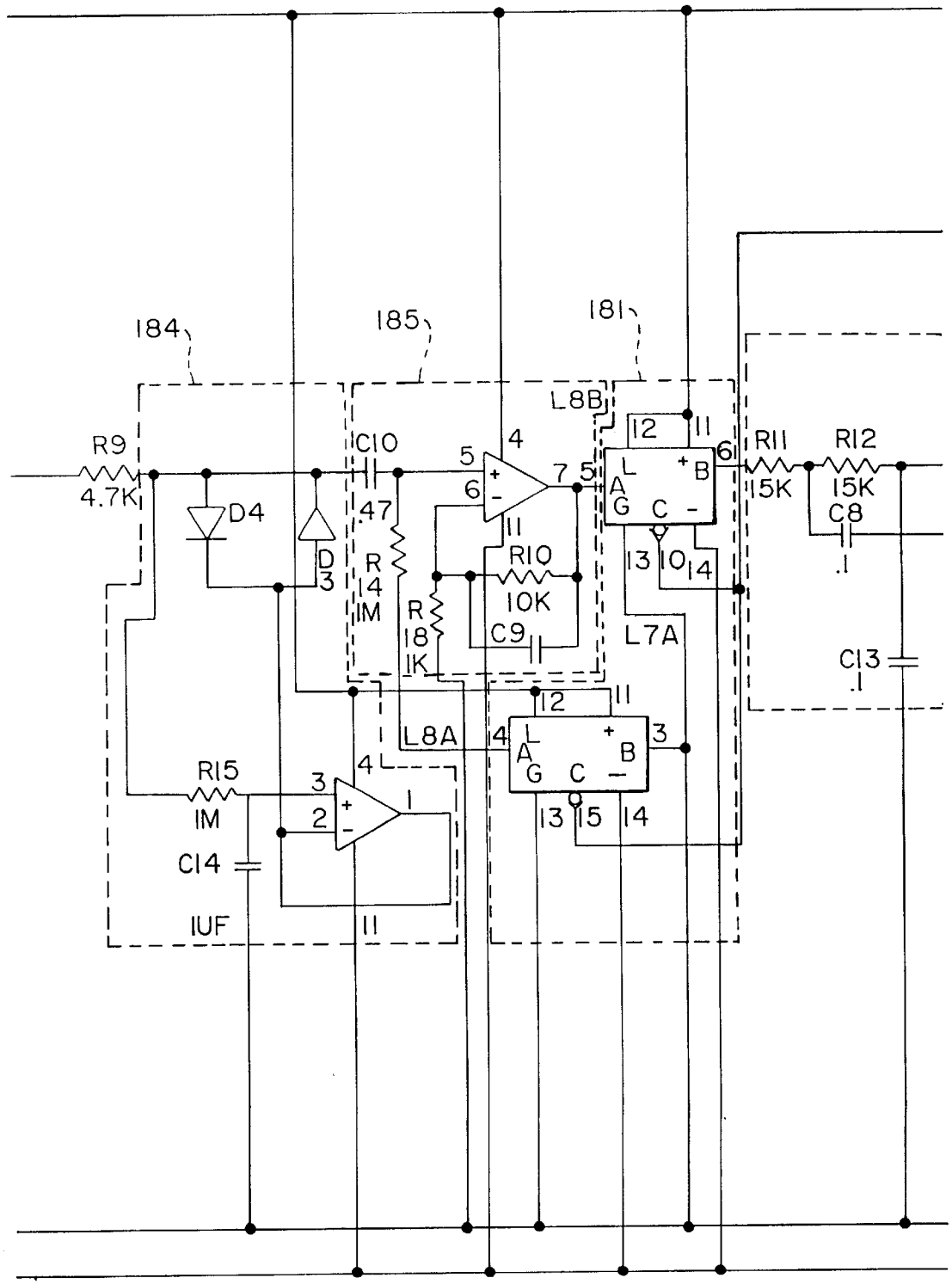
Figure 40C:
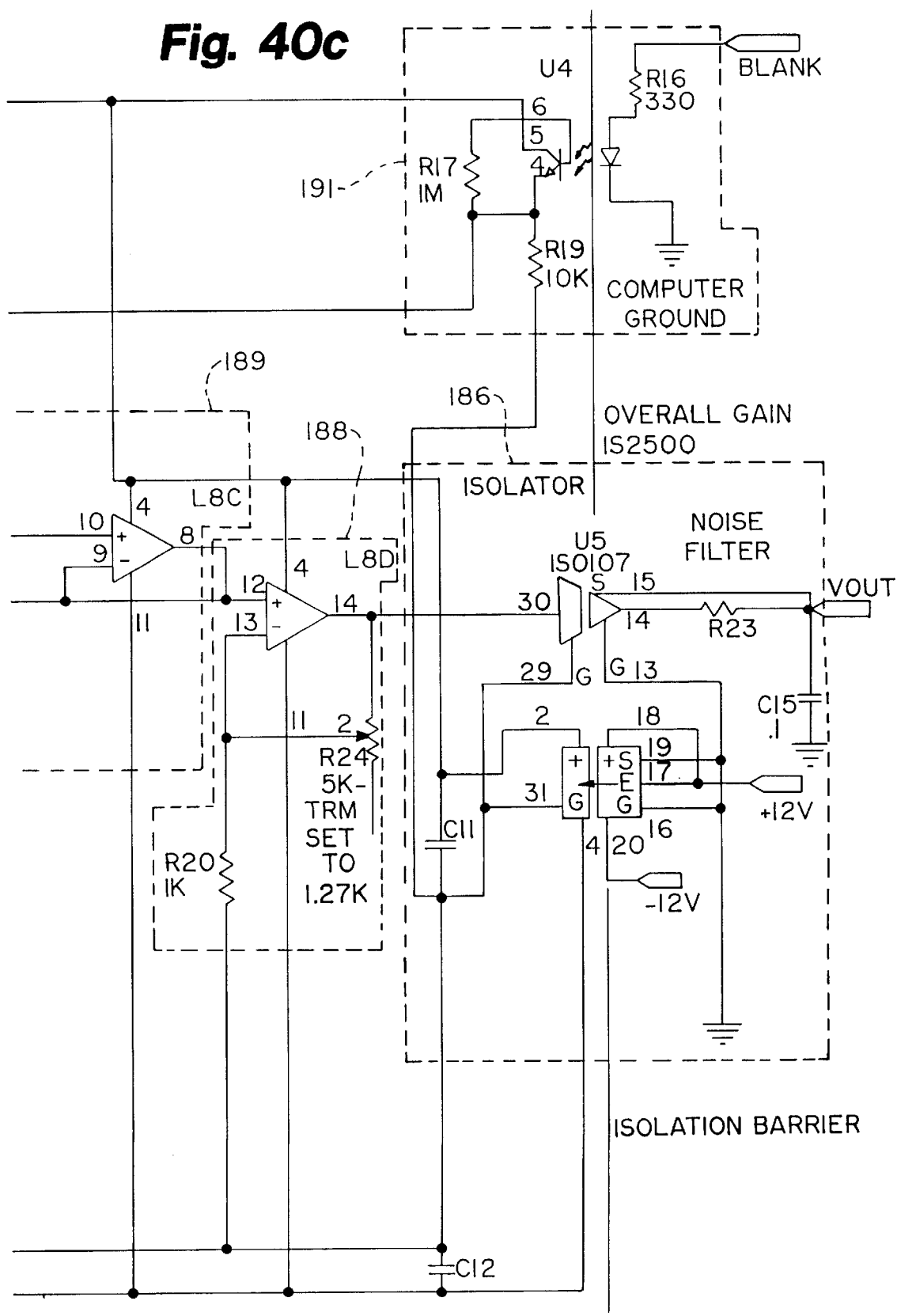
Figure 41:
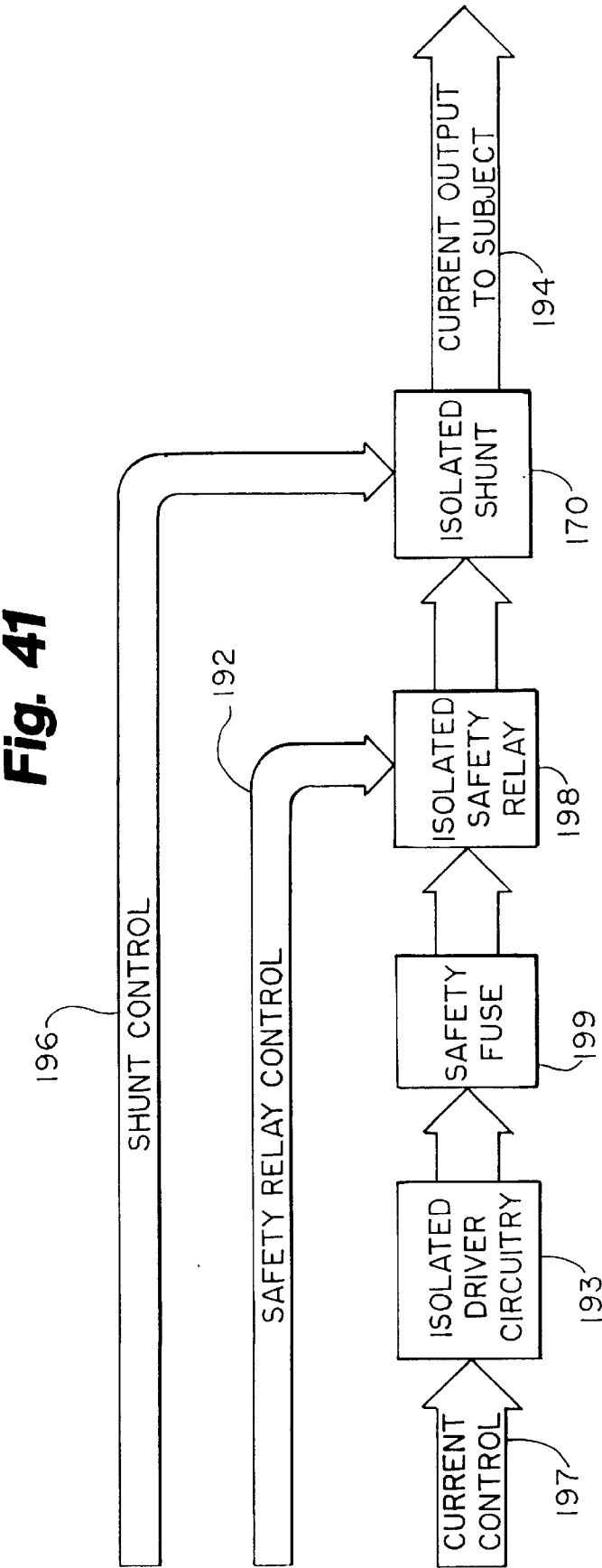
FIG. 41 is a block diagram/flow chart of the isolated driver section of the electronics interface.
Figure 42:
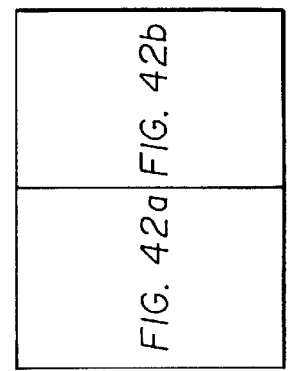
FIG. 42 is a schematic of the isolated driver section of the electronics interface.
Figure 42A:
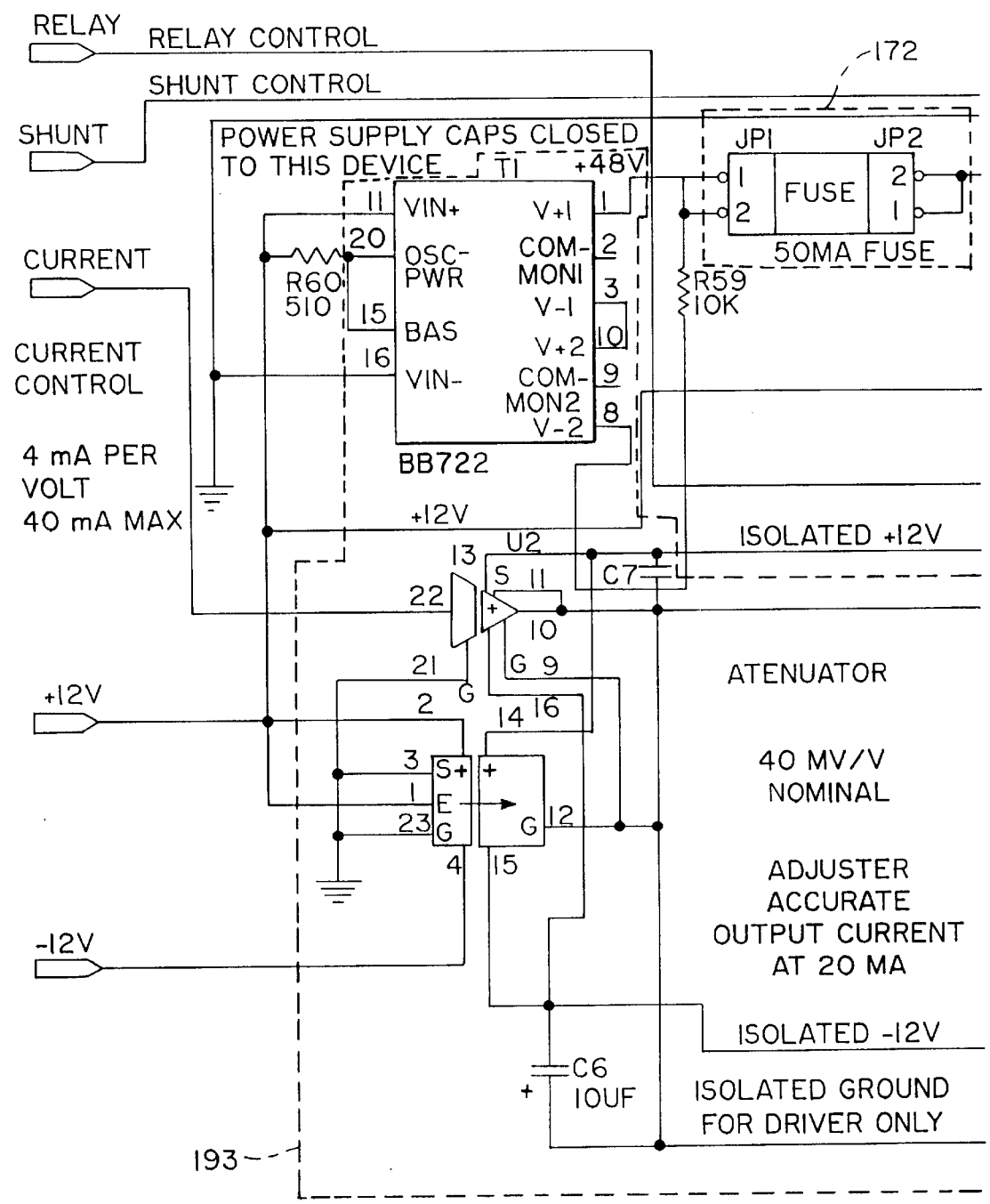
Figure 42B:
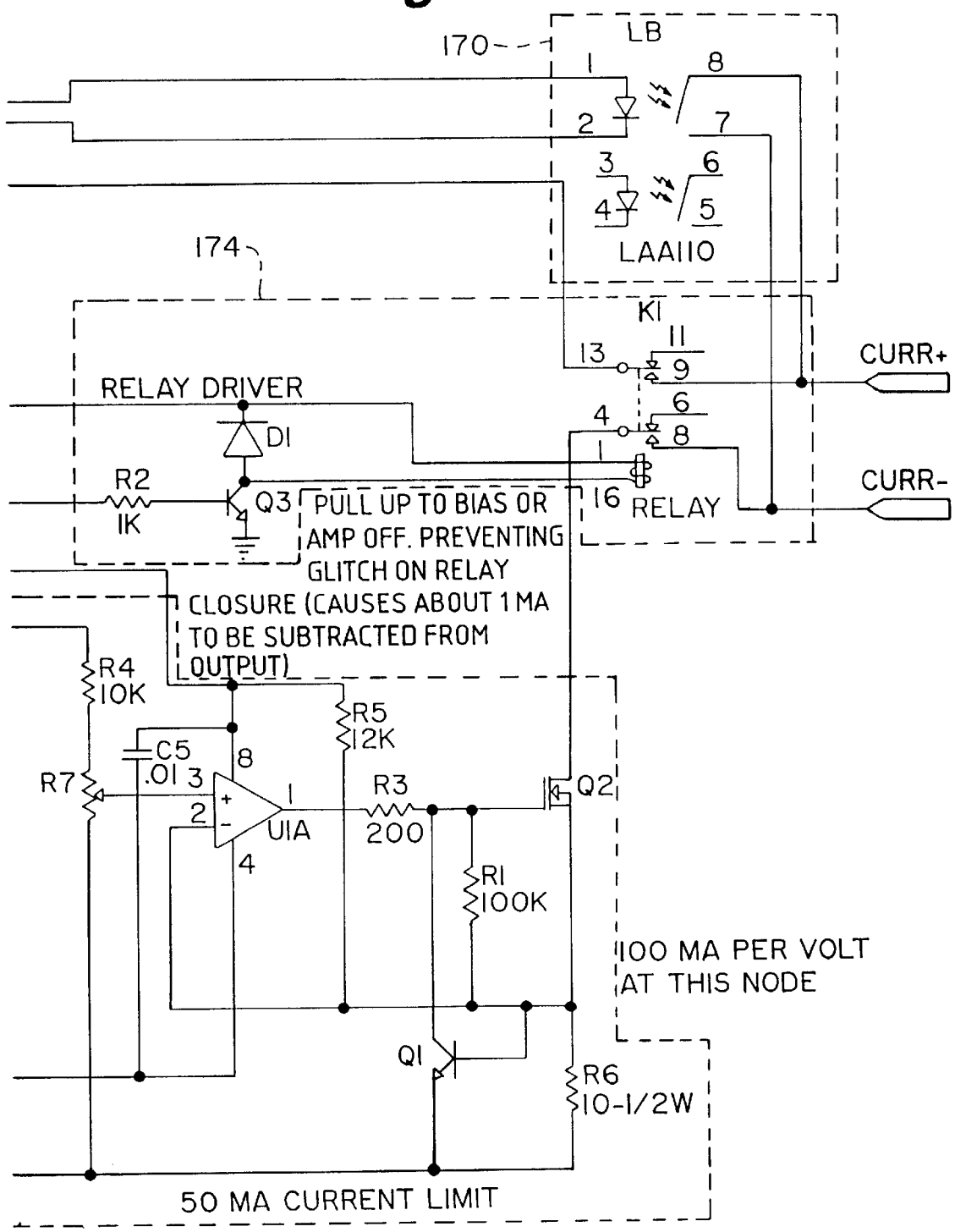
Figure 45A:
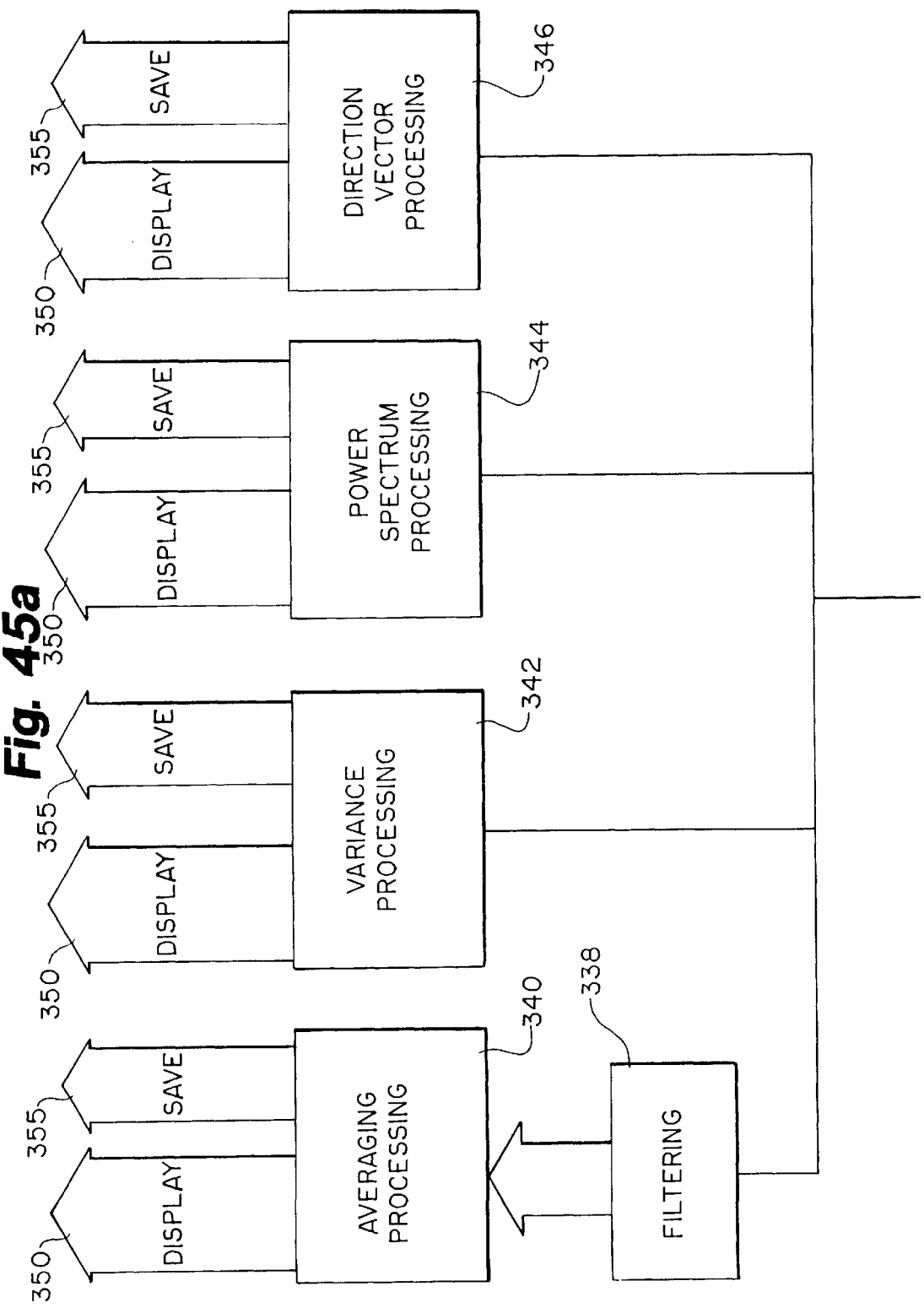
FIG. 45 is a lower-level flow chart of the post-processing software operation.
Figure 45B:
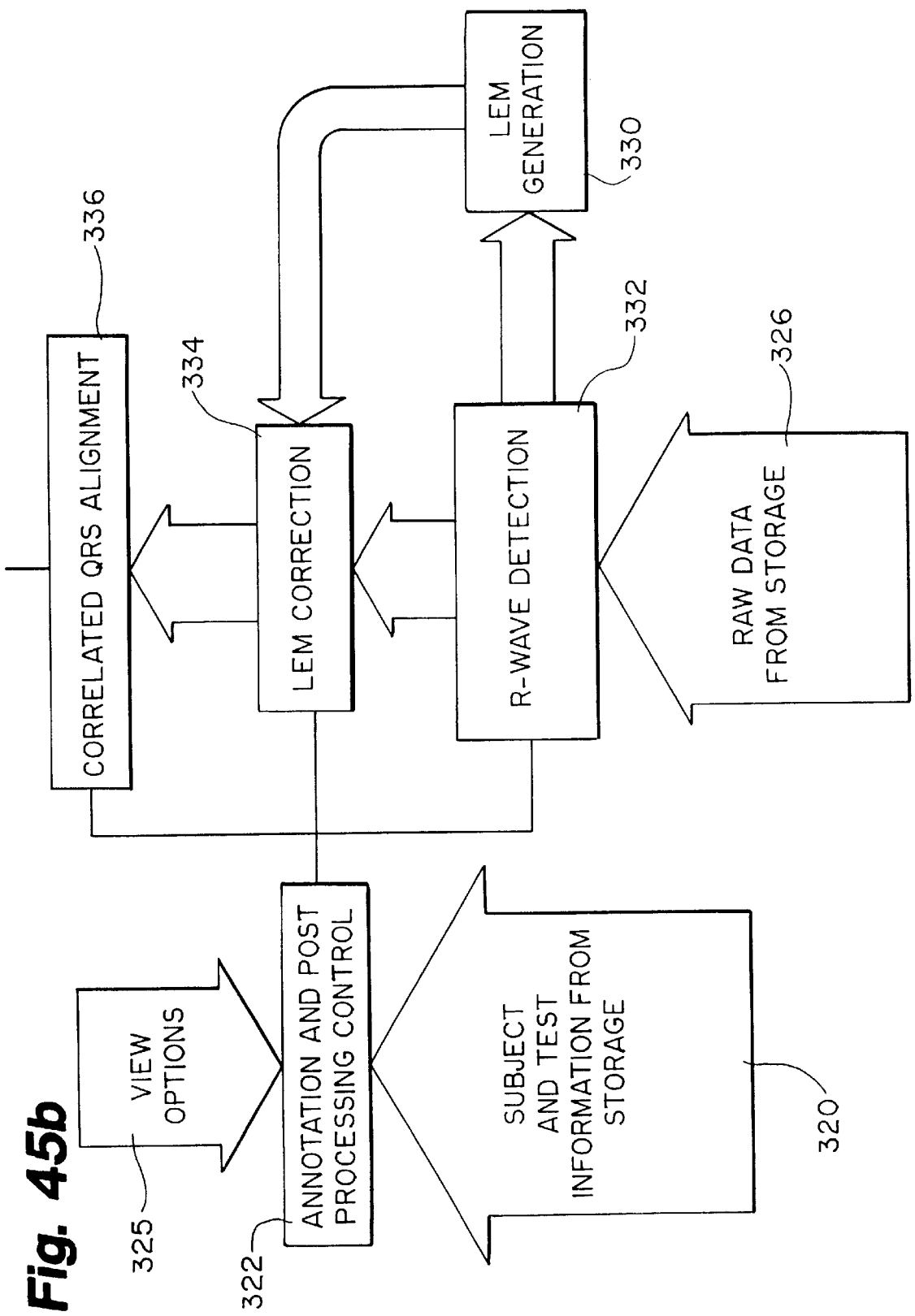
Figure 46:
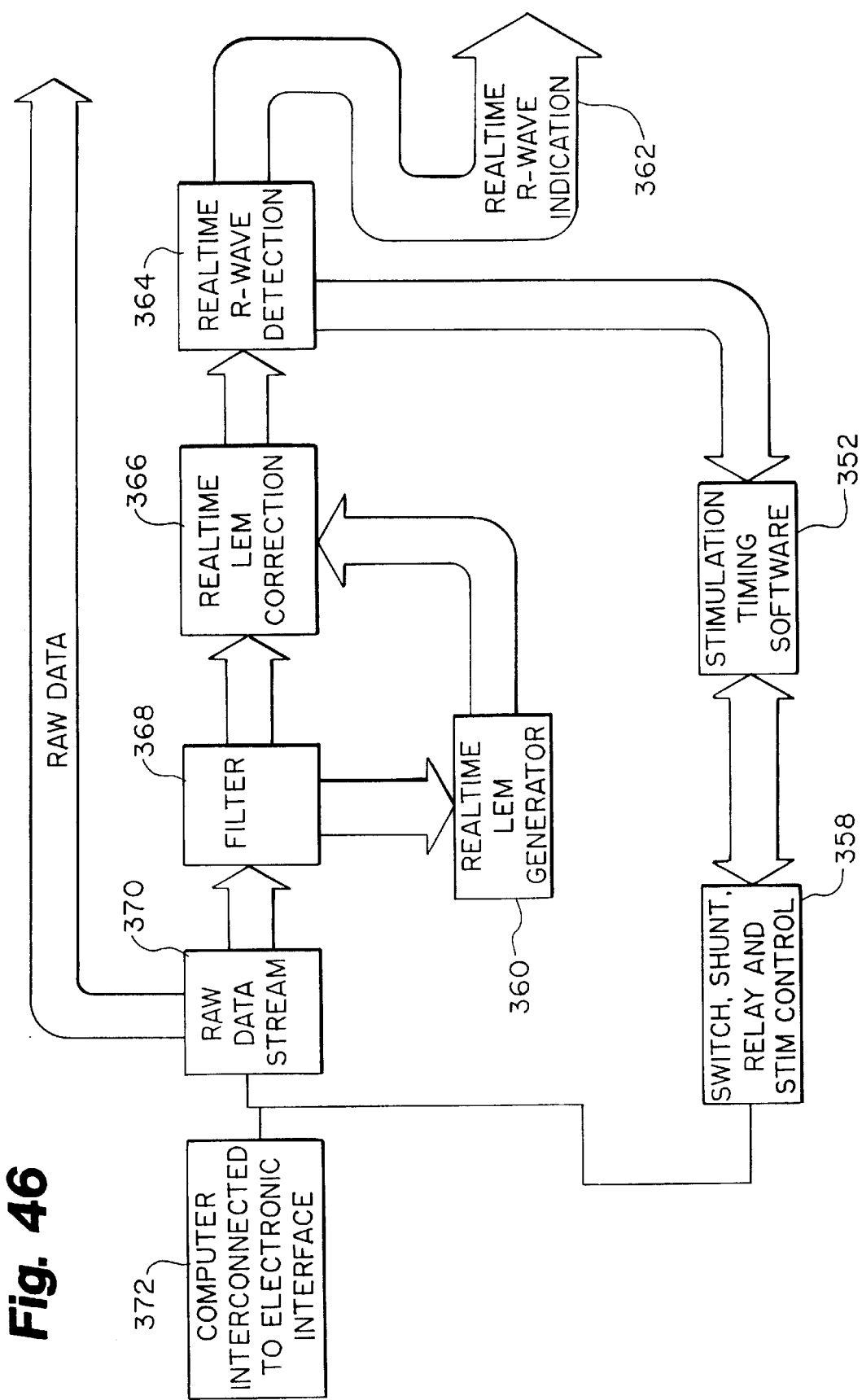
FIG. 46 is a lower-level flow chart of the realtime enter of controls implemented by the software.

What is claimed is:

1. A method for detecting patient susceptibility to arrhythmias comprising the steps of:

providing means for injecting low level electromagnetic energy stimulations into a patient's body suitable to alter at least one cardiac signal to allow a comparison of acquired distinguishable signal differences with at least one other cardiac signal which has not been affected by said injected energy;

connecting a lead system for both sensing the cardiac signals and delivering the injected energy to said means for injecting low level electromagnetic energy into the patient's body, said lead system, comprising a plurality of energy sensing and energy delivery leads and a reference lead; and utilizing sensing improvement means for improving the quality of the sensed electromagnetic energy during the stimulation and acquisition process, said sensing improvement means utilization comprises the steps of:

comprises switch means connected between energy delivery leads so that the switch means is operable relative to the termination of the output current and switches from a high impedance to a low impedance for a short period of time to allow dissipation of any voltage present; and using a fast recovery amplifier method for rapid recovery of the amplifier following stimulation signals.

2. The method of claim 1, further comprising the steps of evaluating baseline noise and continuing the stimulation and data acquisition process until enough data has been acquired to allow statistical noise reduction to a predetermined level.

3. The method of claim 1, in which said sensing improvement means utilization step further comprises the step of providing the energy delivery leads with shunting means connected between said leads.

4. A method for detecting patient susceptibility to arrhythmias comprising the steps of:

providing means for injecting low level electromagnetic energy stimulations into a patient's body suitable to alter at least one cardiac signal to allow a comparison of acquired distinguishable signal differences with at least one other cardiac signal which has not been affected by said injected energy;

connecting a lead system for both sensing the cardiac signals and delivering the injected energy to said means for injecting low level electromagnetic energy into the patient's body, said lead system comprising a plurality of energy sensing and energy delivery leads; and utilizing sensing improvement means for improving the quality of the sensed electromagnetic energy, comprising using a lead effect modeling and correction algorithm which corrects for signal artifacts during stimulation and acquisition cycles during post-processing of acquired signal data.

5. The method of claim 4, in which the lead system connecting step further comprises connection of a body surface reference point with the lead system.

6. The method of claim 5, in which the sensing improvement means utilization comprises the step of using a fast recovery amplifier method for rapid recovery of the amplifier following stimulation signals.

7. The method of claim 6, in which the fast recovery amplifier step comprises the steps of:
configuring an electronic track and hold switch between a pre-switch stage and a post-switch stage of the amplifier so that when the switch is opened, the switch uses a lower capacitance reference point of the differential signal between positive and negative leads; and
configuring the track and hold switch to remain opened during stimulation and a blanking period following stimulation.

8. The method of claim 6, wherein the utilizing sensing improvement means for improving the quality of the sensed electromagnetic energy during the stimulation and acquisition process acquires a reference lead.

9. The method of claim 7, further comprising the steps of:
disengaging the track and hold switch to an open position during stimulation; and
configuring the track and hold switch so that when in an open position the switch provides a hold function that holds the signal level for post-switch stages at a constant output and connects the lower capacitance reference signal to the pre-switch stages.

10. The method of claim 9, further comprising the step of configuring a clamping circuit to engage when the input signal is greater than about ±5 millivolts.

11. The method of claim 7, further comprising the step of filtering the acquired stimulation signal to eliminate possible high frequency, switch-related artifacts.

12. The method of claim 6, in which the fast recovery amplifier performs the steps of:
configuring an electronic track and hold switch between a pre-switch stage and a post-switch stage of the amplifier so that when the switch is closed the switch uses a lower capacitance reference point of the differential signal between positive and negative leads; and
configuring a clamping circuit for switching to an engaged position when the input signal is greater than about ±5 millivolts; and
configuring a clamping circuit to engage when the input signal is greater than about ±5 millivolts.

13. A method for detecting patient susceptibility to arrhythmias comprising the steps of:
providing means for injecting low level electromagnetic energy stimulations into a patient's body suitable to alter at least one cardiac signal to allow a comparison of acquired distinguishable signal differences with at least one other cardiac signal which has not been affected by said injected energy;
connecting a lead system for both sensing the cardiac signals and delivering the injected energy to said means for injecting low level electromagnetic energy into the patient's body, said lead system comprising a plurality of energy sensing and energy delivery leads; and
utilizing sensing improvement means for improving the quality of the sensed electromagnetic energy, comprising using a lead position correction algorithm which corrects for signal artifacts during stimulation and acquisition cycles.

14. A method for detecting patient susceptibility to arrhythmias comprising the steps of:
providing means for injecting low level electromagnetic energy stimulations into a patient's body suitable to alter at least one cardiac signal to allow a comparison of acquired distinguishable signal differences with at least one other cardiac signal which has not been affected by said injected energy;
connecting a lead system for both sensing the cardiac signals and delivering the injected energy to said means for injecting low level electromagnetic energy into the patient's body, said lead system comprising a plurality of energy sensing and energy delivery leads; and
utilizing sensing improvement means for improving the quality of the sensed electromagnetic energy, comprising using a lead position correction algorithm which corrects for signal artifacts during stimulation and acquisition cycles during post-processing of acquired signal data.

15. A method for detecting patient susceptibility to arrhythmias comprising the steps of:
providing means for injecting low level electromagnetic energy stimulations into a patient's body suitable to alter at least one cardiac signal to allow a comparison of acquired distinguishable signal differences with at least one other cardiac signal which has not been affected by said injected energy;
connecting a lead system for both sensing the cardiac signals and delivering the injected energy to said means for injecting low level electromagnetic energy into the patient's body, said lead system comprising a plurality of energy sensing and energy delivery leads; and
utilizing sensing improvement means for improving the quality of the sensed electromagnetic energy, comprising using a muscle response correction algorithm which corrects for signal artifacts during stimulation and acquisition cycles.

16. A method for detecting patient susceptibility to arrhythmias comprising the steps of:
providing means for injecting low level electromagnetic energy stimulations into a patient's body suitable to alter at least one cardiac signal to allow a comparison of acquired distinguishable signal differences with at least one other cardiac signal which has not been affected by said injected energy;
connecting a lead system for both sensing the cardiac signals and delivering the injected energy to said means for injecting low level electromagnetic energy into the patient's body, said lead system comprising a plurality of energy sensing and energy delivery leads; and
utilizing sensing improvement means for improving the quality of the sensed electromagnetic energy, comprising using a muscle response correction algorithm which corrects for signal artifacts during post-processing of acquired signal data.

17. A method for detecting patient susceptibility to arrhythmias comprising the steps of:
providing means for injecting low level electromagnetic energy stimulations into a patient's body suitable to alter at least one cardiac signal to allow a comparison of acquired distinguishable signal differences with at least one other cardiac signal which has not been affected by said injected energy;

connecting a lead system for both sensing the cardiac signals and delivering the injected energy to said means for injecting low level electromagnetic energy into the patient's body, said lead system comprising a plurality of energy sensing and energy delivery leads; and applying a plurality of stimulations during the stimulation and acquisition process, the application of the stimulations being commenced between the T and P waves during a period of low signal level prior to the R-wave detection.

18. A method for detecting patient susceptibility to arrhythmias comprising the steps of:

providing means for injecting low level electromagnetic energy stimulations into a patient's body suitable to alter at least one cardiac signal to allow a comparison of acquired distinguishable signal differences with at least one other cardiac signal which has not been affected by said injected energy;

connecting a lead system for both sensing the cardiac signals and delivering the injected energy to said means for injecting low level electromagnetic energy into the patient's body, said lead system comprising a plurality of energy sensing and energy delivery leads; and applying a plurality of stimulations during the stimulation and acquisition process, and insuring that each of the stimulations have approximately the same energy and duration as the stimulations delivered at other times in the cardiac cycle.

19. A method for detecting patient susceptibility to arrhythmias comprising the steps of:

providing means for injecting low level electromagnetic energy stimulations into a patient's body suitable to alter at least one cardiac signal to allow a comparison of acquired distinguishable signal differences with at least one other cardiac signal which has not been affected by said injected energy;

connecting a lead system for both sensing the cardiac signals and delivering the injected energy to said means for injecting low level electromagnetic energy into the patient's body, said lead system comprising a plurality of energy sensing and energy delivery leads;

providing stimulation signals within a lead effect modeling time period between the T and P waves, at the beginning and periodically throughout the stimulation and acquisition process;

determining the response to the stimulations for a period of up to about 50 milliseconds for each of said stimulations;

creating a lead effect model by combining the response of the stimulations during said determining period to generate a response signal; and utilizing the derived response signal to mathematically attribute electrical artifact and muscle activity.

20. The method of claim 19, in which the determining step comprises removing any baseline signal by subtracting the corresponding waveform having a non-stimulating T-P interval from the current signal.

21. A method for detecting patient susceptibility to arrhythmias comprising the steps of:

providing means for injecting low level electromagnetic energy stimulations into a patient's body suitable to alter at least one cardiac signal to allow a comparison of acquired distinguishable signal differences with at least one other cardiac signal which has not been affected by said injected energy;

connecting a lead system for both sensing the cardiac signals and delivering the injected energy to said means for injecting low level electromagnetic energy into the patient's body, said lead system comprising a plurality of energy sensing and energy delivery leads; and providing stimulation signals within a lead effect modeling time period between the T and P waves, at the beginning and periodically throughout the stimulation and acquisition process.

22. The method of claim 21, further comprising the step of utilizing a baseline shift with a time constant decay.

23. The method of claim 22, in which the baseline shift is determined by comparing samples prior to stimulations during the lead effect modeling time period to samples following the lead effect modeling time period.

24. The method of claim 23, further comprising the step of sampling the decay following the lead effect modeling time period to determine a time constant for the decay.

25. The method of claim 22, in which the decay is determined by determining the decay over about 10 milliseconds.

26. The method of claim 22, in which the decaying baseline shift is mathematically removed from the acquired data following the lead effect modeling time period.

27. The method of claim 22, in which the decaying baseline shift is mathematically removed for up to about 300 milliseconds following the end of the lead effect modeling time period.

28. A method for detecting patient susceptibility to arrhythmias comprising the steps of:

providing means for injecting low level electromagnetic energy stimulations into a patient's body suitable to alter at least one cardiac signal to allow a comparison of acquired distinguishable signal differences with at least one other cardiac signal which has not been affected by said injected energy;

connecting a lead system for both sensing the cardiac signals and delivering the injected energy to said means for injecting low level electromagnetic energy into the patient's body, said lead system comprising a plurality of energy sensing and energy delivery leads;

configuring a plurality of the sensing leads with a fast recovery material for rapid dissipation of any induced energy; and configuring a plurality of the energy delivery leads to have a low impedance.

29. A method for detecting patient susceptibility to arrhythmias comprising the steps of:

providing means for injecting low level electromagnetic energy stimulations into a patient's body suitable to alter at least one cardiac signal to allow a comparison of acquired distinguishable signal differences with at least one other cardiac signal which has not been affected by said injected energy;

connecting a lead system for both sensing the cardiac signals and delivering the injected energy to said means for injecting low level electromagnetic energy into the patient's body, said lead system comprising a plurality of energy sensing and energy delivery leads;

providing the energy delivery leads with shunting means connected between said leads; and providing switch means configured to sense termination of an output current in the energy delivery leads and then switch from a high impedance to a low impedance for a short period of time to allow dissipation of any voltage present.

30. The method of claim 29, in which the switch means switches between an initial high impedance of greater than about 5,000 ohms and a lower impedance of less than about 500 ohms.

31. The method of claim 29, in which the switching between high and low impedances occurs within a time of less than about 1 millisecond.

32. A method for detecting patient susceptibility to arrhythmias comprising the steps of:

providing means for injecting low level electromagnetic energy stimulations into a patient's body suitable to alter at least one cardiac signal to allow a comparison of acquired distinguishable signal differences with at least one other cardiac signal which has not been affected by said injected energy;

connecting a lead system for both sensing the cardiac signals and delivering the injected energy to said means for injecting low level electromagnetic energy into the patient's body, said lead system comprising a plurality of energy sensing and energy delivery leads;

configuring the leads of said lead system at a plurality of external locations on the patient's skin;

maintaining each of the leads of said lead system in the same locations during a time period during which cardiac signals include a detected plurality of stimulated and non-stimulated cardiac signals; and configuring said lead system to sense the spatial direction of cardiac wavefront.

33. The method of claim 32, further comprising the step of determining the magnitude and direction of the cardiac wavefronts.

34. The method of claim 32, further comprising the step of processing and analyzing the directional signals.

35. The method of claim 34, further comprising the step of comparing and displaying the directional data of stimulated and non-stimulated cardiac signals as acquired by leads which have remained stationary throughout the time period of the transmission and detection of the signals resulting in the processed cardiac signals.

36. The method of claim 35, in which the comparing step is performed for cardiac signals throughout all locations of the QRST complex independent of signal amplitude.

37. A method for detecting patient susceptibility to arrhythmias, using a computer and a computer display, the method comprising:

installing on said computer a diagnostic software program comprising data files and application programs, the software program providing computer-generated and displayed graphical user interfaces (GUIs);

connecting an electronics interface to said computer, and further connecting a lead system by a connector to said electronic interface;

applying a plurality of electrodes, said electrodes being a part of said lead system, to a patient upon whom a diagnostic test to determine susceptibility to arrythmia is to be performed;

selecting, from a drop-down menu of said computer-generated GUI, a command to perform a test sequence;

selecting, from a further computer-generated GUI, an existing patient profile or a new patient profile;

configuring, from a subsequent computer-generated GUI, patient information, subpacing pulse configuration, test duration, sensitivity, and deviation limit;

observing, in real time, resulting QRS complex events;

biasing, by delivering a subpacing current to the cardiac tissue of the patient, to effect a QRS complex event at a predetermined time, said predetermined time being determined by the software program; and analyzing the resultant data, with assistance of the software program, to determine the patient's susceptibility to arrhythmia.

38. A method for detecting patient susceptibility to arrhythmias, using a computer and a computer display, the method comprising:

installing on said computer a diagnostic software program comprising data files and application programs, the software program providing computer-generated and displayed graphical user interfaces (GUIs);

connecting an electronics interface to said computer, and further connecting a lead system by a connector to said electronic interface;

applying a plurality of electrodes, said electrodes being a part of said lead system, to a patient upon whom a diagnostic test to determine susceptibility to arrythmia is to be performed;

biasing, by delivering a subpacing current to the cardiac tissue of the patient, to effect a QRS complex event at a predetermined time, said predetermined time being determined by the software program;

determining the presentation of the acquired data by selecting features available from the computer-generated GUI;

filtering the acquired data by selecting features available from the computer-generated GUI;

observing the acquired data by selecting features available from the computer-generated GUI;

manipulating the acquired data by selecting features available from the computer-generated GUI;

simulating the acquired data by selecting features available from the computer-generated GUI;

displaying a graph of the average of the acquired data on the computer-generated GUI;

displaying a biased average of the acquired data on the computer-generated GUI; and graphing the difference between a biased and an unbiased QRS complex average on the computer-generated GUI;

analyzing the resultant data, with assistance of the software program, to determine the patient's susceptibility to arrhythmia.

39. A method for detecting patient susceptibility to arrhythmias, using a computer and a computer display, the method comprising:

installing on said computer a diagnostic software program comprising data files and application programs, the software program providing computer-generated and displayed graphical user interfaces (GUIs);

connecting an electronics interface to said computer, and further connecting a lead system by a connector to said electronic interface;

applying a plurality of electrodes, said electrodes being a part of said lead system, to a patient upon whom a diagnostic test to determine susceptibility to arrythmia is to be performed;

biasing, by delivering a subpacing current to the cardiac tissue of the patient, to effect a QRS complex event at a predetermined time, said predetermined time being determined by the software program;

analyzing the resultant data, with assistance of the software program, to determine the patient's susceptibility to arrhythmia;

saving the acquired data to an internal disk by selecting features available from the computer-generated GUI;

saving the acquired data to an external disk by selecting features available from the computer-generated GUI;

retrieving data from an external disk by selecting features available from the computer-generated GUI;

saving protocol steps for future use by selecting features available from the computer-generated GUI; and retrieving selected protocols from past use by selecting features available from the computer-generated GUI.

\* \* \* \* \*